(12) United States Patent
Medoff

(10) Patent No.: US 7,708,214 B2
(45) Date of Patent: May 4, 2010

(54) FIBROUS MATERIALS AND COMPOSITES

(75) Inventor: Marshall Medoff, Brookline, MA (US)

(73) Assignee: Xyleco, Inc., Woburn, MA (US)

( * ) Notice: Subject to any disclaimer, the term of this patent is extended or adjusted under 35 U.S.C. 154(b) by 107 days.

(21) Appl. No.: 11/453,951

(22) Filed: Jun. 15, 2006

(65) Prior Publication Data

US 2007/0045456 A1 Mar. 1, 2007

Related U.S. Application Data

(63) Continuation-in-part of application No. PCT/US2006/010648, filed on Mar. 23, 2006.

(60) Provisional application No. 60/711,057, filed on Aug. 24, 2005.

(51) Int. Cl.
| | |
|---|---|
| B27K 7/00 | (2006.01) |
| B27K 9/00 | (2006.01) |
| B27L 11/00 | (2006.01) |
| D21D 1/30 | (2006.01) |

(52) U.S. Cl. .......................... 241/28; 241/30
(58) Field of Classification Search .................. 241/73, 241/28, 30
See application file for complete search history.

(56) References Cited

U.S. PATENT DOCUMENTS

| | | |
|---|---|---|
| 1,824,221 A | 9/1931 | Mason |
| 2,516,847 A | 8/1950 | Boehm |
| 2,519,442 A | 8/1950 | Delorme et al. |
| 2,558,378 A | 6/1951 | Petry |
| 2,635,976 A | 4/1953 | Meiler et al. |
| 2,658,828 A | 11/1953 | Pattilloch |
| 2,665,261 A | 1/1954 | Baker |
| 2,680,102 A | 6/1954 | Becher |
| 2,757,150 A | 7/1956 | Heritage |
| 2,789,903 A | 4/1957 | Lukman et al. |
| 2,935,763 A | 5/1960 | Newman et al. |
| 3,308,218 A | 3/1967 | Wiegand et al. |
| 3,309,444 A | 3/1967 | Schueler |
| 3,493,527 A | 2/1970 | Schueler |
| 3,516,953 A | 6/1970 | Wood |
| 3,596,314 A | 8/1971 | Krugler |
| 3,645,939 A | 2/1972 | Gaylord |
| 3,671,615 A | 6/1972 | Price |
| 3,697,364 A | 10/1972 | Boustany |
| 3,709,845 A | 1/1973 | Boustany |
| 3,718,536 A | 2/1973 | Downs et al. |

(Continued)

FOREIGN PATENT DOCUMENTS

AU 47811/90 1/1989

(Continued)

OTHER PUBLICATIONS

Abstract of JP 09267441, filed Oct. 14, 1997, in Chemical Abstracts 127:294599.

(Continued)

*Primary Examiner*—Bena Miller
(74) *Attorney, Agent, or Firm*—Celia H. Leber

(57) ABSTRACT

Fibrous materials, compositions that include fibrous materials, and uses of the fibrous materials and compositions are disclosed. For example, the fibrous materials can be operated on by a microorganism to produce ethanol or a by-product, such as a protein or lignin.

16 Claims, 14 Drawing Sheets

U.S. PATENT DOCUMENTS

| | | |
|---|---|---|
| 3,836,412 A | 9/1974 | Boustany et al. |
| 3,878,143 A | 4/1975 | Baumann et al. |
| 3,888,810 A | 6/1975 | Shinomura |
| 3,943,079 A | 3/1976 | Hamed |
| 3,956,541 A | 5/1976 | Pringle |
| 3,956,555 A | 5/1976 | McKean |
| 3,985,927 A | 10/1976 | Norris et al. |
| 4,005,162 A | 1/1977 | Bucking |
| 4,016,232 A | 4/1977 | Pringle |
| 4,020,212 A | 4/1977 | Erickson |
| 4,033,913 A | 7/1977 | Sunden |
| 4,045,603 A | 8/1977 | Smith |
| 4,056,591 A | 11/1977 | Goettler et al. |
| 4,058,580 A | 11/1977 | Flanders |
| 4,097,648 A | 6/1978 | Pringle |
| 4,112,038 A | 9/1978 | Garner |
| 4,113,908 A | 9/1978 | Shinomura |
| 4,115,497 A | 9/1978 | Halmo Rolls et al. |
| 4,145,389 A | 3/1979 | Smith |
| 4,168,251 A | 9/1979 | Schinzel et al. |
| 4,187,352 A | 2/1980 | Klobbie |
| 4,188,259 A | 2/1980 | Mamers et al. |
| 4,203,876 A | 5/1980 | Dereppe et al. |
| 4,204,010 A | 5/1980 | Kramm et al. |
| 4,228,116 A | 10/1980 | Colombo et al. |
| 4,239,679 A | 12/1980 | Rolls et al. |
| 4,244,847 A | 1/1981 | Posiviata et al. |
| 4,244,903 A | 1/1981 | Schnause |
| 4,248,743 A | 2/1981 | Goettler |
| 4,248,820 A | 2/1981 | Haataja |
| 4,250,222 A | 2/1981 | Mavel et al. |
| 4,263,184 A | 4/1981 | Leo et al. |
| 4,265,846 A | 5/1981 | Shen et al. |
| 4,273,688 A | 6/1981 | Porzel et al. |
| 4,277,428 A | 7/1981 | Luck et al. |
| 4,279,790 A | 7/1981 | Nakajima |
| 4,281,039 A | 7/1981 | Miura et al. |
| 4,290,988 A | 9/1981 | Nopper et al. |
| 4,303,019 A | 12/1981 | Haataja et al. |
| 4,305,901 A | 12/1981 | Prince et al. |
| 4,311,554 A | 1/1982 | Herr |
| 4,311,621 A | 1/1982 | Nishizawa et al. |
| 4,318,351 A | 3/1982 | Munk |
| 4,323,625 A | 4/1982 | Coran et al. |
| 4,328,136 A | 5/1982 | Blount |
| 4,359,534 A | 11/1982 | Kurtzman et al. |
| 4,368,268 A | 1/1983 | Gong |
| 4,376,144 A | 3/1983 | Goettler |
| 4,382,108 A | 5/1983 | Carroll et al. |
| 4,393,020 A | 7/1983 | Li et al. |
| 4,400,470 A | 8/1983 | Zeikus et al. |
| 4,414,267 A | 11/1983 | Coran et al. |
| 4,420,351 A | 12/1983 | Lussi et al. |
| 4,426,470 A | 1/1984 | Wessling et al. |
| 4,433,813 A * | 2/1984 | Whatton et al. .......... 241/21 |
| 4,440,708 A | 4/1984 | Haataja et al. |
| 4,454,091 A | 6/1984 | Chion et al. |
| 4,455,709 A | 6/1984 | Zanini |
| 4,480,035 A | 10/1984 | Roychodhury |
| 4,481,701 A | 11/1984 | Hewitt |
| 4,491,553 A | 1/1985 | Yamada et al. |
| 4,503,115 A | 3/1985 | Hemels et al. |
| 4,505,869 A | 3/1985 | Nishibori |
| 4,506,037 A | 3/1985 | Suzuki et al. |
| 4,508,595 A | 4/1985 | Gasland |
| 4,511,656 A | 4/1985 | Gong |
| 4,520,530 A | 6/1985 | Pinto |
| 4,551,294 A | 11/1985 | Wottka et al. |
| 4,559,376 A | 12/1985 | Kubat |
| 4,562,218 A | 12/1985 | Fornadel et al. |
| 4,594,372 A | 6/1986 | Natov et al. |
| 4,597,928 A | 7/1986 | Terentiev et al. |
| 4,608,922 A | 9/1986 | Pohl |
| 4,609,624 A | 9/1986 | Rothlisberger |
| 4,610,900 A | 9/1986 | Nishibori |
| 4,612,286 A | 9/1986 | Sherman et al. |
| 4,624,890 A | 11/1986 | Lloyd et al. |
| 4,632,170 A | 12/1986 | Pohl |
| 4,645,631 A | 2/1987 | Hegenstaller et al. |
| 4,659,754 A | 4/1987 | Edwards et al. |
| 4,663,225 A | 5/1987 | Farley et al. |
| 4,674,414 A | 6/1987 | Nülle et al. |
| 4,686,251 A | 8/1987 | Ostermann et al. |
| 4,687,793 A | 8/1987 | Motegi et al. |
| 4,713,291 A | 12/1987 | Sasaki et al. |
| 4,716,062 A | 12/1987 | Klein |
| 4,717,742 A | 1/1988 | Beshay |
| 4,734,236 A | 3/1988 | Davis |
| 4,737,532 A | 4/1988 | Fujita et al. |
| 4,738,723 A | 4/1988 | Frizzell et al. |
| 4,746,688 A | 5/1988 | Bistak et al. |
| 4,769,109 A | 9/1988 | Tellvik et al. |
| 4,769,274 A | 9/1988 | Tellvik et al. |
| 4,791,020 A | 12/1988 | Kokta |
| 4,810,445 A | 3/1989 | Lamb, Sr. et al. |
| 4,812,410 A | 3/1989 | Lawford |
| 4,818,604 A | 4/1989 | Tock |
| 4,833,181 A | 5/1989 | Narukawa et al. |
| 4,840,902 A | 6/1989 | Lawford |
| 4,840,903 A | 6/1989 | Wu |
| 4,851,458 A | 7/1989 | Hopperdietzel |
| 4,865,788 A | 9/1989 | Davis |
| 4,874,095 A | 10/1989 | Warych |
| 4,894,192 A | 1/1990 | Warych |
| 4,911,700 A | 3/1990 | Makoui et al. |
| 4,915,764 A | 4/1990 | Miani |
| 4,927,579 A | 5/1990 | Moore |
| 4,929,498 A | 5/1990 | Suskind et al. |
| 4,935,182 A | 6/1990 | Ehner et al. |
| 4,960,548 A | 10/1990 | Ikeda et al. |
| 4,963,603 A | 10/1990 | Felegi, Jr. et al. |
| 4,968,463 A | 11/1990 | Levasseur |
| 4,973,440 A | 11/1990 | Tamura et al. |
| 4,978,489 A | 12/1990 | Radvan et al. |
| 4,988,478 A | 1/1991 | Held |
| 5,002,713 A | 3/1991 | Palardy et al. |
| 5,008,310 A | 4/1991 | Beshay |
| 5,009,586 A | 4/1991 | Pallmann |
| 5,028,266 A | 7/1991 | Rettenmaier |
| 5,028,539 A | 7/1991 | Ingram et al. |
| 5,057,167 A | 10/1991 | Gersbeck |
| 5,064,692 A | 11/1991 | Hofmann et al. |
| 5,075,057 A | 12/1991 | Hoedl |
| 5,075,359 A | 12/1991 | Castagna et al. |
| 5,082,605 A | 1/1992 | Brooks et al. |
| 5,084,135 A | 1/1992 | Brooks et al. |
| 5,087,400 A | 2/1992 | Theuveny |
| 5,088,910 A | 2/1992 | Goforth et al. |
| 5,093,058 A | 3/1992 | Harmon et al. |
| 5,096,046 A | 3/1992 | Goforth et al. |
| 5,096,406 A | 3/1992 | Brooks et al. |
| 5,100,545 A | 3/1992 | Brooks |
| 5,100,603 A | 3/1992 | Neefe |
| 5,100,791 A | 3/1992 | Spindler et al. |
| 5,102,055 A * | 4/1992 | Buschmann et al. .......... 241/5 |
| 5,104,411 A | 4/1992 | Makoui et al. |
| 5,120,776 A | 6/1992 | Raj et al. |
| 5,124,519 A | 6/1992 | Roy et al. |
| 5,134,023 A | 7/1992 | Hsu |
| 5,134,944 A | 8/1992 | Keller et al. |
| 5,137,668 A | 8/1992 | Lamb, Sr. |
| 5,155,147 A | 10/1992 | Dietz et al. |
| 5,177,009 A | 1/1993 | Kampen |
| 5,183,837 A | 2/1993 | Lepori et al. |

| Patent | Date | Inventor |
|---|---|---|
| 5,194,461 A | 3/1993 | Berquist et al. |
| 5,196,069 A | 3/1993 | Cullingford et al. |
| 5,198,074 A | 3/1993 | Villavicencio et al. |
| 5,213,021 A | 5/1993 | Goforth et al. |
| 5,254,617 A | 10/1993 | Inoue et al. |
| 5,268,074 A | 12/1993 | Brooks et al. |
| 5,277,758 A | 1/1994 | Brooks et al. |
| 5,284,610 A | 2/1994 | Tai |
| 5,285,973 A | 2/1994 | Goforth et al. |
| 5,298,102 A | 3/1994 | Pohl |
| 5,331,087 A | 7/1994 | Menges |
| 5,348,871 A | 9/1994 | Scott et al. |
| 5,350,370 A | 9/1994 | Jackson et al. |
| 5,351,895 A | 10/1994 | Brooks et al. |
| 5,366,790 A | 11/1994 | Liebel |
| 5,370,999 A | 12/1994 | Stuart |
| 5,372,878 A | 12/1994 | Saito |
| 5,372,939 A | 12/1994 | Lastick et al. |
| 5,374,474 A | 12/1994 | Pratt et al. |
| 5,380,180 A | 1/1995 | Lamb, Sr. |
| 5,406,768 A | 4/1995 | Giuseppe et al. |
| 5,421,205 A | 6/1995 | Pohl |
| 5,424,202 A | 6/1995 | Ingram et al. |
| 5,432,000 A | 7/1995 | Young, Sr. et al. |
| 5,437,766 A | 8/1995 | Van Phan et al. |
| 5,439,542 A | 8/1995 | Liebel |
| 5,439,749 A | 8/1995 | Klasell et al. |
| 5,441,801 A | 8/1995 | Deaner et al. |
| 5,480,602 A | 1/1996 | Nagaich |
| 5,486,553 A | 1/1996 | Deaner et al. |
| 5,487,989 A | 1/1996 | Fowler et al. |
| 5,497,594 A | 3/1996 | Giuseppe et al. |
| 5,498,478 A | 3/1996 | Hansen et al. |
| 5,498,766 A | 3/1996 | Stuart et al. |
| 5,516,472 A | 5/1996 | Laver |
| 5,516,585 A | 5/1996 | Young, Sr. et al. |
| 5,518,677 A | 5/1996 | Deaner et al. |
| 5,539,027 A | 7/1996 | Deaner et al. |
| 5,540,244 A | 7/1996 | Brooks et al. |
| 5,543,205 A | 8/1996 | Liebel |
| 5,547,745 A | 8/1996 | Hansen et al. |
| 5,554,520 A | 9/1996 | Fowler et al. |
| 5,558,933 A | 9/1996 | Anthony |
| 5,571,618 A | 11/1996 | Hansen et al. |
| 5,574,094 A | 11/1996 | Malucelli et al. |
| 5,582,682 A | 12/1996 | Ferretti |
| 5,582,847 A | 12/1996 | Peterson et al. |
| 5,585,155 A | 12/1996 | Heikkila et al. |
| 5,614,570 A | 3/1997 | Hansen et al. |
| 5,628,830 A | 5/1997 | Brink |
| 5,637,502 A | 6/1997 | Scott et al. |
| 5,643,359 A | 7/1997 | Soroushian et al. |
| 5,643,635 A | 7/1997 | Ahn et al. |
| 5,663,216 A | 9/1997 | Tomka |
| 5,677,154 A | 10/1997 | Van Draanen et al. |
| 5,682,015 A | 10/1997 | Harben |
| 5,695,874 A | 12/1997 | Deaner et al. |
| 5,705,216 A | 1/1998 | Tyson |
| 5,733,758 A | 3/1998 | Nguyen |
| 5,735,916 A | 4/1998 | Lucas et al. |
| 5,746,958 A | 5/1998 | Gustafsson et al. |
| 5,753,474 A | 5/1998 | Ramey |
| 5,759,680 A | 6/1998 | Brooks et al. |
| 5,767,177 A | 6/1998 | Omente et al. |
| 5,773,138 A | 6/1998 | Seethamraju et al. |
| 5,779,164 A | 7/1998 | Chieffalo et al. |
| 5,791,262 A | 8/1998 | Knight et al. |
| 5,819,491 A | 10/1998 | Davis |
| 5,821,111 A | 10/1998 | Grady et al. |
| 5,824,246 A | 10/1998 | Reetz |
| 5,827,607 A | 10/1998 | Deaner et al. |
| 5,837,506 A | 11/1998 | Lynd et al. |
| 5,851,469 A | 12/1998 | Muller et al. |
| 5,871,161 A | 2/1999 | Nishibori |
| 5,874,263 A | 2/1999 | Holtzapple et al. |
| 5,876,641 A | 3/1999 | LeClair et al. |
| 5,882,564 A | 3/1999 | Puppin |
| 5,882,905 A | 3/1999 | Saha et al. |
| 5,888,806 A | 3/1999 | Nguyen |
| 5,932,334 A | 8/1999 | Deaner et al. |
| 5,932,456 A | 8/1999 | Van Drannen et al. |
| 5,942,424 A | 8/1999 | Woodward et al. |
| 5,948,505 A | 9/1999 | Puppin |
| 5,948,524 A | 9/1999 | Seethamraju et al. |
| 5,952,105 A | 9/1999 | Medoff et al. |
| 5,962,307 A | 10/1999 | Holtzapple et al. |
| 5,973,035 A | 10/1999 | Medoff et al. |
| 5,981,067 A | 11/1999 | Seethamraju et al. |
| 5,985,429 A | 11/1999 | Plummer et al. |
| 6,004,668 A | 12/1999 | Deaner et al. |
| 6,007,656 A | 12/1999 | Heikkilä et al. |
| 6,015,611 A | 1/2000 | Deaner et al. |
| 6,015,612 A | 1/2000 | Deaner et al. |
| 6,015,703 A | 1/2000 | White et al. |
| 6,043,392 A | 3/2000 | Holtzapple et al. |
| 6,054,207 A | 4/2000 | Finley |
| 6,090,595 A | 7/2000 | Foody et al. |
| 6,102,690 A | 8/2000 | Ingram et al. |
| 6,106,944 A | 8/2000 | Heikkila et al. |
| 6,122,877 A | 9/2000 | Hendrickson et al. |
| 6,130,076 A | 10/2000 | Ingram |
| 6,207,729 B1 | 3/2001 | Medoff et al. |
| 6,210,792 B1 | 4/2001 | Seethamraju et al. |
| 6,258,175 B1 | 7/2001 | Lightner |
| 6,258,876 B1 | 7/2001 | Medoff et al. |
| 6,270,883 B1 | 8/2001 | Sears et al. |
| 6,270,893 B1 | 8/2001 | Young, Sr. et al. |
| 6,333,181 B1 | 12/2001 | Ingram et al. |
| 6,346,160 B1 | 2/2002 | Puppin |
| 6,357,197 B1 | 3/2002 | Serino et al. |
| 6,409,841 B1 | 6/2002 | Lombard |
| 6,410,302 B1 | 6/2002 | Träff et al. |
| 6,419,828 B1 | 7/2002 | Russo, Jr. |
| 6,420,626 B1 | 7/2002 | Erspamer et al. |
| 6,425,979 B1 | 7/2002 | Hansen et al. |
| 6,448,307 B1 | 9/2002 | Medoff et al. |
| 6,509,180 B1 | 1/2003 | Verser et al. |
| 6,521,087 B2 | 2/2003 | Hansen et al. |
| 6,555,350 B2 | 4/2003 | Ahring et al. |
| 6,620,503 B2 | 9/2003 | Qin et al. |
| 6,660,506 B2 | 12/2003 | Nguyen et al. |
| 6,670,035 B2 | 12/2003 | Pittman et al. |
| 6,692,825 B2 | 2/2004 | Qin et al. |
| 6,703,227 B2 | 3/2004 | Jakel et al. |
| 6,730,249 B2 | 5/2004 | Sears et al. |
| 6,743,507 B2 | 6/2004 | Barlow et al. |
| 6,746,976 B1 | 6/2004 | Urankar et al. |
| 6,824,682 B2 | 11/2004 | Branson |
| 6,824,729 B2 | 11/2004 | Oin et al. |
| 6,835,560 B2 | 12/2004 | Greene |
| 6,846,657 B2 | 1/2005 | Heikkilä et al. |
| 6,855,180 B1 | 2/2005 | Pinatti et al. |
| 6,855,182 B2 | 2/2005 | Sears |
| 6,908,995 B2 | 6/2005 | Blount |
| 6,927,048 B2 | 8/2005 | Verser et al. |
| 6,962,722 B2 | 11/2005 | Dawley et al. |
| 6,969,781 B2 | 11/2005 | Graef et al. |
| 7,026,152 B2 | 4/2006 | Ingram et al. |
| 7,074,603 B2 | 7/2006 | Verser et al. |
| 7,135,308 B1 | 11/2006 | Bush et al. |
| 7,138,257 B2 | 11/2006 | Galli et al. |
| 7,160,714 B2 * | 1/2007 | Matano .................... 435/262 |
| 7,169,821 B2 | 1/2007 | Branson |
| 7,307,108 B2 | 12/2007 | Medoff et al. |
| 2002/0010229 A1 | 1/2002 | Medoff et al. |
| 2002/0019614 A1 | 2/2002 | Woon et al. |

| | | |
|---|---|---|
| 2002/0137154 A1 | 9/2002 | Ingram et al. |
| 2003/0021915 A1 | 1/2003 | Rohatgi et al. |
| 2003/0032702 A1 | 2/2003 | Medoff et al. |
| 2003/0054500 A1 | 3/2003 | Ingram et al. |
| 2003/0109011 A1 | 6/2003 | Hood et al. |
| 2003/0121380 A1 | 7/2003 | Cowell et al. |
| 2003/0125688 A1 | 7/2003 | Keane et al. |
| 2003/0157675 A1 | 8/2003 | Otero et al. |
| 2003/0187102 A1 | 10/2003 | Medoff et al. |
| 2003/0207064 A1 | 11/2003 | Bunyan et al. |
| 2004/0005461 A1 | 1/2004 | Nagle et al. |
| 2004/0172878 A1 | 9/2004 | Krylowicz et al. |
| 2004/0187863 A1 | 9/2004 | Langhauser |
| 2004/0219649 A1 | 11/2004 | Olsen et al. |
| 2004/0231661 A1 | 11/2004 | Griffin et al. |
| 2004/0253696 A1 | 12/2004 | Grichko |
| 2005/0069998 A1 | 3/2005 | Perdices et al. |
| 2005/0106734 A1 | 5/2005 | Richard et al. |
| 2005/0112739 A1 | 5/2005 | Golubkov |
| 2005/0136520 A1 | 6/2005 | Kinley et al. |
| 2005/0164355 A1 | 7/2005 | Vlasenko et al. |
| 2005/0191736 A1 | 9/2005 | Brown et al. |
| 2005/0272134 A1 | 12/2005 | Hughes |
| 2005/0277574 A1 | 12/2005 | Niedbala et al. |
| 2006/0005279 A1 | 1/2006 | Dotson et al. |
| 2006/0014260 A1 | 1/2006 | Fan et al. |
| 2006/0026715 A1 | 2/2006 | Hood et al. |
| 2006/0053514 A1 | 3/2006 | Wu et al. |
| 2006/0057264 A1 | 3/2006 | Hughes et al. |
| 2006/0088922 A1 | 4/2006 | Yang et al. |
| 2006/0105442 A1 | 5/2006 | Wu et al. |
| 2006/0127999 A1 | 6/2006 | Verser et al. |
| 2006/0234364 A1 | 10/2006 | Rajgarhia et al. |
| 2006/0246563 A1 | 11/2006 | Eroma et al. |
| 2006/0251764 A1 | 11/2006 | Abbas et al. |
| 2006/0292677 A1 | 12/2006 | Ostrander |
| 2007/0031953 A1 | 2/2007 | Dunson, Jr. et al. |
| 2007/0045456 A1 | 3/2007 | Medoff |

FOREIGN PATENT DOCUMENTS

| | | |
|---|---|---|
| EP | 0 161 766 | 11/1985 |
| EP | 0 161 766 A1 | 11/1985 |
| EP | 0 330 729 A1 | 9/1988 |
| EP | 0 409 525 A2 | 7/1990 |
| GB | 2104903 | 3/1983 |
| GB | 2171953 | 9/1986 |
| JP | 61-243805 | 10/1986 |
| JP | 10-130672 | 5/1998 |
| WO | WO 92/07022 | 4/1992 |
| WO | WO 93/03135 | 2/1993 |
| WO | WO 93/05186 | 3/1993 |
| WO | WO 94/08027 | 4/1994 |
| WO | WO 96/13468 | 5/1996 |
| WO | WO 96/13551 | 5/1996 |
| WO | WO 96/37627 | 11/1996 |
| WO | WO 97/06942 | 2/1997 |
| WO | WO 97/10352 | 3/1997 |
| WO | WO 97/18173 | 5/1997 |
| WO | WO 97/42307 | 11/1997 |
| WO | WO 98/58071 | 12/1998 |
| WO | WO 99/11453 | 3/1999 |
| WO | WO 99/23138 | 5/1999 |
| WO | WO 00/29183 | 5/2000 |
| WO | WO 00/34567 | 6/2000 |
| WO | WO 01/32715 A1 | 5/2001 |
| WO | WO 02/025/59 A1 | 1/2002 |
| WO | WO 02/14039 A1 | 2/2002 |
| WO | WO 02/38786 A1 | 5/2002 |
| WO | WO 02/057317 A1 | 7/2002 |
| WO | WO 03/062430 A1 | 7/2003 |
| WO | WO 2005/003319 A2 | 1/2005 |
| WO | WO 2005/054487 A1 | 6/2005 |
| WO | WO 2005/069849 A2 | 8/2005 |
| WO | WO 2005/079190 A2 | 9/2005 |
| WO | WO 2005/111214 A1 | 11/2005 |
| WO | WO 2005/113459 A1 | 12/2005 |
| WO | WO 2005/118828 A1 | 12/2005 |
| WO | WO 2006/031757 A1 | 3/2006 |
| WO | WO 2006/096527 A2 | 9/2006 |
| WO | WO 2006/101584 A2 | 9/2006 |
| WO | WO 2006/114095 A1 | 11/2006 |
| WO | WO 2006/119052 A2 | 11/2006 |
| WO | WO 2006/128304 A1 | 12/2006 |
| WO | WO 2007/005646 A2 | 1/2007 |
| WO | WO 2007/009463 A2 | 1/2007 |

OTHER PUBLICATIONS

Kokta et al., "Composites of Polyvinyl Chloride-Wood Fibers. I. Effect of Isocyanate as a Bonding Agent", Polym. Plast. Technol. Eng. 29(1&2), 1990, pp. 87-118.

Kokta et al., "Composites of Polyvinyl Chloride-Wood Fibers. III. Effect of Silane as Coupling Agent", Journal of Vinyl Technology, Sep. 1990, vol. 12, No. 3, pp. 146-153.

Kokta et al., "Composites of Poly(Vinyl Chloride) and Wood Fibers. Part II: Effect of Chemical Treatment", Polymer Composites, Apr. 1990, vol. 11, No. 2, pp. 84-89.

Yam et al., "Composites From Compounding Wood Fibers With Recycled High Density Polyethylene", Polymer Engineering and Science, Mid-Jun. 1990, vol. 30, No. 11, pp. 693-699.

Raj et al., "Use of Wood Fibers as Filler in Common Thermoplastic Studies on Mechanical Properties", Science and Engineering of Composite Materials, vol. 1, No. 3, 1989, pp. 85-98.

Raj et al., "Use of Wood Fibers in Thermoplastics. VII. The Effect of Coupling Agents in Polyethylene-Wood Fiber Composites", Journal of Applied Polymer Science, vol. 37, (1989), pp. 1089-1103.

Maldas et al., "Composites of Polyvinyl Chloride-Wood Fibers: IV. Effect of the Nature of Fibers", Journal of Vinyl Technology, Jun. 1989, vol. 11, No. 2, pp. 90-98.

Zadorecki et al., "Future Prospects for Wood Cellulose as Reinforcement in Organic Polymer Composites", Polymer Composites, Apr. 1989, vol. 10, No. 2, pp. 69-77.

Dalvag et al., "The Efficiency of Cellulosic Fillers in Common Thermoplastics. Part II. Filling with Process Aids and Coupling Agents", International Journal of Polymeric Materials, 1985, vol. 11, pp. 9-38.

Klason et al., "The Efficiency of Cellulosic Fillers in Common Thermoplastics. Part I. Filling Without Processing Aids or Coupling Agents", International Journal of Polymeric Materials, Mar. 1984, pp. 159-187.

Woodhams et al., "Wood Fibers as Reinforcing Fillers for Polyolefins", Polymer Engineering and Science, Oct. 1984, vol. 24, No. 15, pp. 1166-1171.

Kokta et al., "Use of Wood Fibers in Thermoplastic Composites", Polymer Composites, Oct. 1983, vol. 4, No. 4, pp. 229-232.

Kokta et al., "Use of Grafted Wood Fibers in Thermoplastic Composites V. Polystyrene", pp. 85-96.

* cited by examiner

VACUUM SOURCE 50

FIBROUS MATERIALS AND COMPOSITES

CROSS REFERENCE TO RELATED APPLICATIONS

This application is a continuation-in-part (CIP) of, and claims the benefit of priority from, International Application No. PCT/US2006/010648, filed on Mar. 23, 2006, which claims priority from U.S. Provisional Patent Application Ser. No. 60/711,057, filed Aug. 24, 2005, the entire contents of each application is hereby incorporated by reference herein in its entirety.

TECHNICAL FIELD

This invention relates to fibrous materials and to compositions.

BACKGROUND

Fibrous materials, e.g., cellulosic and lignocellulosic materials, are produced, processed, and used in large quantities in a number of applications. Often such fibrous materials are used once, and then discarded as waste.

Various fibrous materials, their uses and applications have been described in U.S. Pat. Nos. 6,448,307, 6,258,876, 6,207,729, 5,973,035 and 5,952,105. The entire disclosure of each of the patents of this paragraph is incorporated by reference herein.

SUMMARY

Generally, this invention relates to fibrous materials, methods of making fibrous materials, compositions that include fibrous materials (e.g., composites that include the fibrous materials and a resin, or compositions that include the fibrous materials and bacteria and/or an enzyme), and to uses of the same. For example, the compositions can be used to make ethanol, or a by-product, such as a protein or lignin, or applied to a structure as insulation.

Any of the fibrous materials disclosed herein can be used in combination with any of the fibrous materials, resins, additives, or other components disclosed in U.S. Pat. Nos. 6,448,307, 6,258,876, 6,207,729, 5,973,035 and 5,952,105. In turn, these fibrous materials and/or components can be used in any of the applications, products, procedures, et cetera disclosed in any of these patents or in this application.

The fibrous materials or compositions that include the fibrous materials can be, e.g., associated with, blended with, adjacent to, surrounded by, or within a structure or carrier (e.g., a netting, a membrane, a flotation device, a bag, a shell, or a biodegradable substance). Optionally, the structure or carrier may itself be made from a fibrous material, or of a composition that includes a fibrous material. In some embodiments, the fibrous material is combined with a material, such as a protic acid, that enhances the rate of biodegradation of the fibrous material. In some embodiments, the fibrous material is combined with a material that retards degradation of the fibrous material, such as a buffer.

The ratio of fibrous materials to the other components of the compositions will depend upon the nature of the components, and can be readily adjusted for a specific product application.

Any of the fibrous materials described herein, including any of the fibrous materials made by any of the methods described herein, can be used, e.g., to form composites with resin, or can be combined with bacteria and/or one or more enzymes to produce a valuable product, such as a fuel (e.g., ethanol, a hydrocarbon, or hydrogen).

In one aspect, the invention features methods of making fibrous materials. The methods include shearing a fiber source to provide a first fibrous material, and passing the first fibrous material through a first screen having an average opening size of 1.59 mm or less (1/16 inch, 0.0625 inch) to provide a second fibrous material. The fiber source can, e.g., be cut into pieces or strips of confetti-like material prior to the shearing.

In some embodiments, the average opening size of the first screen is less than 0.79 mm (1/32 inch, 0.03125 inch), e.g., less than 0.40 mm (1/64 inch, 0.015625 inch), less than 0.20 mm (1/128 inch, 0.0078125 inch), or even less than 0.10 mm (1/256 inch, 0.00390625 inch).

In specific implementations, the shearing is performed with a rotary knife cutter. If desired, the shearing can be performed while the fiber source is dry (e.g., having less than 0.25 percent by weight absorbed water), hydrated, or even while the fiber source is partially or fully submerged in a liquid, such as water or isopropanol.

The second fibrous material can, e.g., be collected in a bin having a pressure below nominal atmospheric pressure, e.g., at least 10 percent below nominal atmospheric pressure, at least 50 percent below nominal atmospheric pressure, or at least 75 percent below nominal atmospheric pressure.

The second fibrous material can, e.g., be sheared once or numerous times, e.g., twice, thrice, or even more, e.g., ten times. Shearing can "open up" and/or "stress" the fibrous materials, making the materials more dispersible, e.g., in a solution or in a resin.

The second fibrous material can be, e.g., sheared and the resulting fibrous material passed through the first screen.

The second fibrous material can be sheared, and the resulting fibrous material passed through a second screen having an average opening size less than the first screen, providing a third fibrous material.

A ratio of an average length-to-diameter ratio of the second fibrous material to an average length-to-diameter ratio of the third fibrous material can be, e.g., less than 1.5, less than 1.4, less than 1.25, or even less than 1.1.

The second fibrous can be, e.g., passed through a second screen having an average opening size less than the first screen.

The shearing and passing can be, e.g., performed concurrently.

The second fibrous material can have an average length-to-diameter ratio of, e.g., greater than 10/1, greater than 25/1, or even greater than 50/1.

For example, an average length of the second fibrous material can be between 0.5 mm and 2.5 mm, e.g., between 0.75 mm and 1.0 mm. For example, an average width of the second fibrous material can be between 5 µm and 50 µm, e.g., between 10 µm and 30 µm.

A standard deviation of a length of the second fibrous material can be less than 60 percent of an average length of the second fibrous material, e.g., less than 50 percent of an average length of the second fibrous material.

In some embodiments, a BET surface area of the second fibrous material is greater than 0.5 m$^2$/g, e.g., greater than 1.0 m$^2$/g, greater than 1.5 m$^2$/g, greater than 1.75 m$^2$/g, greater than 2.5 m$^2$/g, greater than 10.0 m$^2$/g, greater than 25.0 m$^2$/g, greater than 50.0 m$^2$/g, or even greater than 100.0 m$^2$/g.

In some embodiments, a porosity of the second fibrous material is greater than 25 percent, e.g., greater than 50 percent, greater than 75 percent, greater than 85 percent, greater than 90 percent, greater than 92 percent, greater than 95 percent, or even greater than 99 percent.

In specific embodiments, the screen is formed by interweaving monofilaments.

The fiber source can include, e.g., a cellulosic material, a lignocellulosic material.

In some embodiments, the fiber source includes a blend of fibers, e.g., fibers derived from a paper source and fibers derived from a textile source, e.g., cotton.

In another aspect, the invention features methods of making fibrous materials that include shearing a fiber source to provide a first fibrous material; and passing the fibrous material through a first screen to provide a second fibrous material. A ratio of an average length-to-diameter ratio of the first fibrous material to an average length-to-diameter of the second fibrous material is less than 1.5.

In another aspect, the invention features methods of making fibrous materials that include shearing a fiber source to provide a first fibrous material; passing the fibrous material through a first screen to provide a second fibrous material; and then shearing the second fibrous material again to provide a third fibrous material.

In another aspect, the invention features composites or compositions made from any of the fibrous materials described herein. For example, compositions can include any of the fibrous materials described herein and a bacterium and/or an enzyme. The compositions that include any of the fibrous materials described herein and the bacterium and/or enzyme can be in a dry state, or they can include a liquid, such as water.

For example, the composite can be in the form of a stepping stool, pipes, panels, decking materials, boards, housings, sheets, blocks, bricks, poles, fencing, members, doors, shutters, awnings, shades, signs, frames, window casings, backboards, flooring, tiles, railroad ties, trays, tool handles, stalls, films, wraps, tapes, boxes, baskets, racks, casings, binders, dividers, walls, mats, frames, bookcases, sculptures, chairs, tables, desks, toys, games, pallets, wharves, piers, boats, masts, septic tanks, automotive panels, computer housings, above- and below-ground electrical casings, furniture, picnic tables, benches, shelters, trays, hangers, servers, caskets, book covers, canes and crutches.

In another aspect, the invention features fibrous materials having an average length-to-diameter ratio of greater than 5, and having a standard deviation of a fiber length of less than sixty percent of an average fiber length.

For example, the average length-to-diameter ratio can be greater than 10/1, e.g., greater than 15/1, greater than 25/1, greater than 35/1, greater than 45/1, or even greater than 50/1.

For example, the average length can be between 0.5 mm and 2.5 mm.

In another aspect, the invention features methods of making fibrous materials that include shearing a fiber source to provide a first fibrous material; collecting the first fibrous material; and then shearing the first fibrous to provide a second fibrous material.

In another aspect, the invention features methods of making a useful material, such as a fuel. The methods include shearing a fiber source to provide a first fibrous material; passing the first fibrous material through a first screen having an average opening size of about 1.59 mm or less (1/16 inch, 0.0625 inch) to provide a second fibrous material; and combining the second fibrous material with a bacterium and/or enzyme, the bacterium and/or enzyme utilizing the second fibrous material to produce a fuel that includes hydrogen, an alcohol, an organic acid and/or a hydrocarbon.

The alcohol can be, e.g., methanol, ethanol, propanol, isopropanol, butanol, ethylene glycol, propylene glycol, 1,4-butane diol, glycerin, or mixtures of these alcohols; the organic acid can be, e.g., malonic acid, succinic acid, glutaric acid, oleic acid, linoleic acid, glycolic acid, lactic acid, γ-hydroxybutyric acid, or mixtures of these acids; and the hydrocarbon can be, e.g., methane, ethane, propane, isobutene, pentane, n-hexane, or mixtures of these hydrocarbons.

Prior to combining with the bacterium and/or enzyme, any of the fibrous materials described herein can be hydrolyzed to break down higher molecular weight carbohydrates into lower molecular weight carbohydrates.

In another aspect, the invention features methods of making a useful material, such as a fuel, by shearing a fiber source or a fibrous material, and then combining it with a bacterium and/or an enzyme. For example, the fiber source can be sheared once to provide a fibrous material, and then the fibrous material can be combined with a bacterium and/or an enzyme to make the useful material.

In another aspect, the invention features methods of densifying fibrous compositions. The methods include shearing a fiber source to provide a fibrous material; combining the fibrous material with a bacterium and/or enzyme to provide a fibrous material composition; encapsulating the composition in a substantially gas impermeable material; and removing entrapped gas from the encapsulated composition to densify the composition. For example, the gas impermeable material can be in the form of a bag, and the composition can be densified by evacuating air from the bag, and then sealing the bag.

In another aspect, the invention features composites that include a fibrous material, a resin and a dye.

For example, the fibrous material can have an average length-to-diameter ratio of greater than 5, and a standard deviation of a fiber length of less than sixty percent of an average fiber length.

In some embodiments, the composite additionally includes a pigment.

In some implementations, the dye soaked into or surfaced on the fibers.

In another aspect, the invention features methods of making composites that include dyeing a fibrous material; combining the fibrous material with a resin; and forming a composite from the combination.

In another aspect, the invention features methods of making composite that include adding a dye to a resin to provide a dye/resin combination; combining the dye/resin combination with a fibrous material; and forming a composite from the dye/resin combination and fibrous material.

The term "fibrous material", as used herein, is a material that includes numerous loose, discrete and separable fibers. For example, a fibrous material can be prepared from a poly-coated paper or a bleached Kraft paper fiber source by shearing, e.g., with a rotary knife cutter.

The term "screen", as used herein, means a member capable of sieving material according to size, e.g., a perforated plate, cylinder or the like, or a wire mesh or cloth fabric.

Embodiments and/or aspects can have any one of, or combinations of, the following advantages. The fibrous materials are opened up and/or stressed, making the materials more dispersible, e.g., in a solution or in a resin, and making them more susceptible to chemical, enzymatic or biological attack. The fibrous materials can have, e.g., a relatively narrow length and/or length-to-diameter ratio distribution, such that their properties are consistently defined. For example, when blended with a molten resin or a solution, the fibers of the fibrous materials can modify the rheology of the molten resin or solution in a consistent and predicable manner, e.g., resulting in resin/fibrous material combinations that are, e.g., easier to mold and extrude. For example, the fibrous materials can easily pass through small openings or channels, such as those found in or associated with injection molds, e.g., gates or hot runners. Parts molded from such fibrous materials can exhibit a good surface finish, e.g., with few visible speckles of large particles and/or agglomerated particles.

All publications, patent applications, patents, and other references mentioned herein are incorporated by reference in their entirety for all that they contain.

Other features and advantages of the invention will be apparent from the following detailed description, and from the claims.

DESCRIPTION OF DRAWINGS

FIG. 10A being a photograph of a polycoated paper container, and FIG. 10B being a photograph of unbleached Kraft paper rolls.

DETAILED DESCRIPTION

Figure 1:
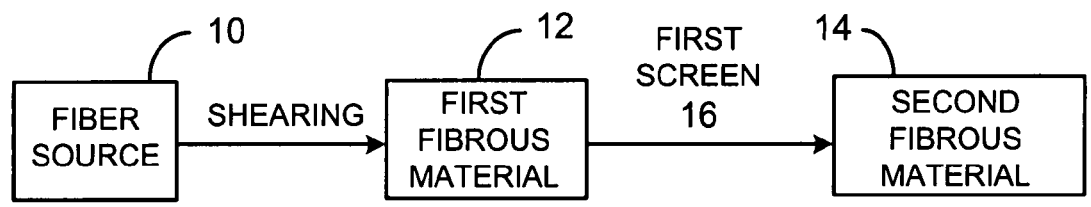
FIG. 1 is block diagram illustrating conversion of a fiber source into a first and second fibrous material.

Referring to FIG. 1, a fiber source 10 is sheared, e.g., in a rotary knife cutter, to provide a first fibrous material 12. The first fibrous material 12 is passed through a first screen 16 having an average opening size of 1.59 mm or less (1/16 inch, 0.0625 inch) to provide a second fibrous material 14. If desired, fiber source 10 can be cut prior to the shearing, e.g., with a shredder. For example, when a paper is used as the fiber source 10, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of fiber source 10 and the passing of the resulting first fibrous material 12 through first screen 16 are performed concurrently. The shearing and the passing can also be performed in a batch-type process.

Figure 2:
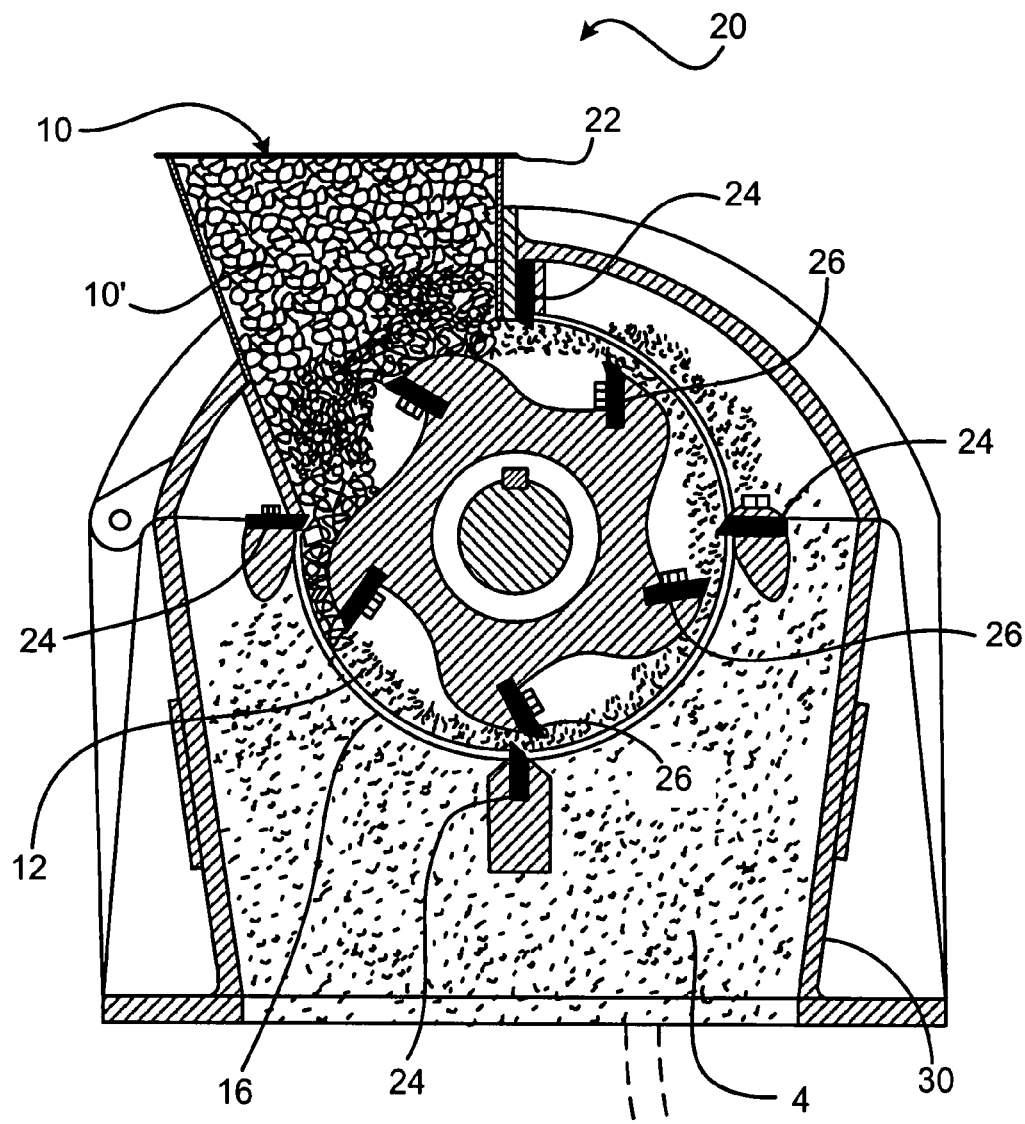
FIG. 2 is a cross-sectional view of a rotary knife cutter.
Figure 4:
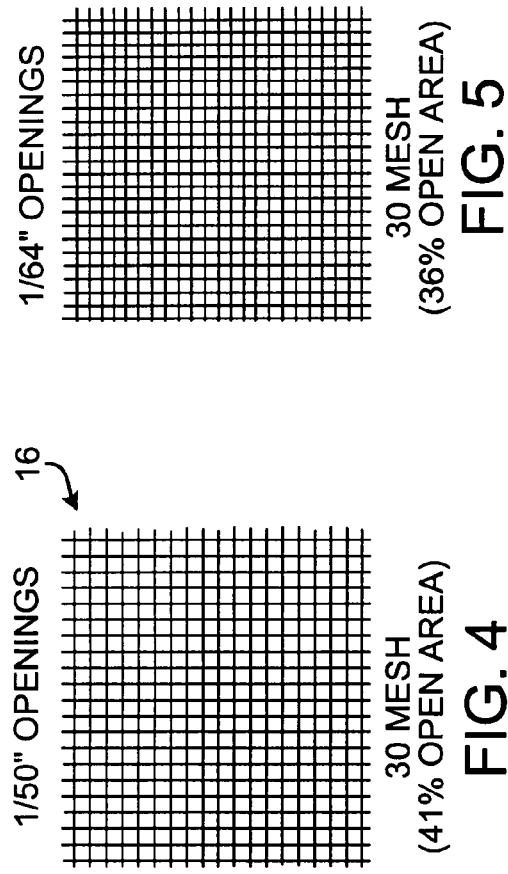
FIGS. 3-8 are top views of a variety of screens made from monofilaments.
Figure 3:
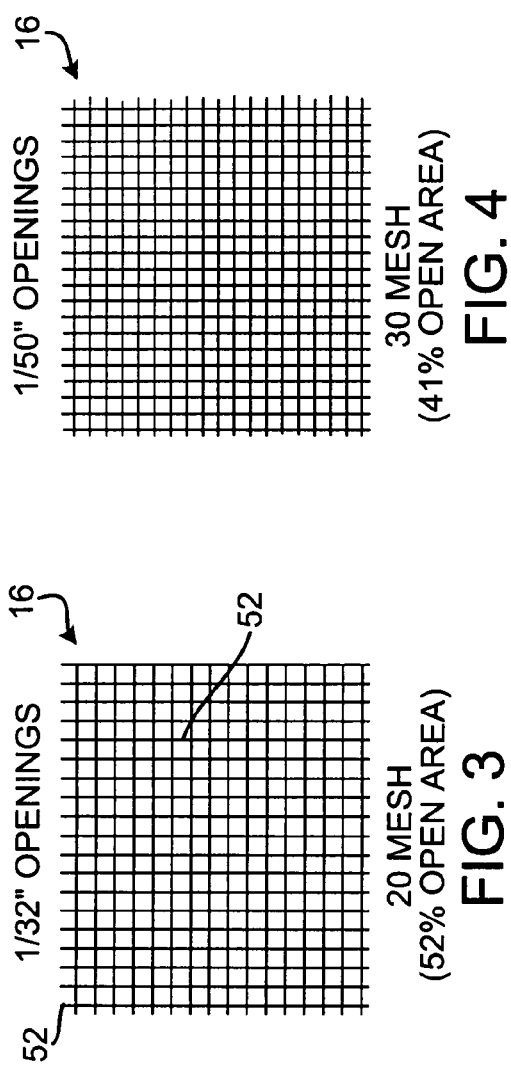
Figure 5:
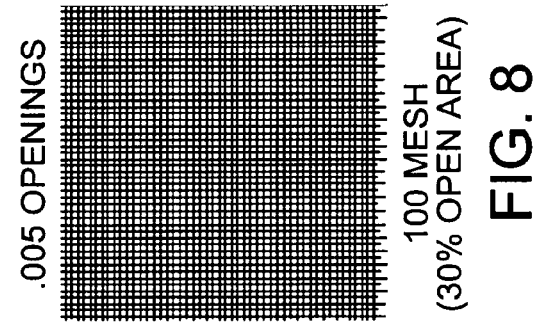
Figure 8:
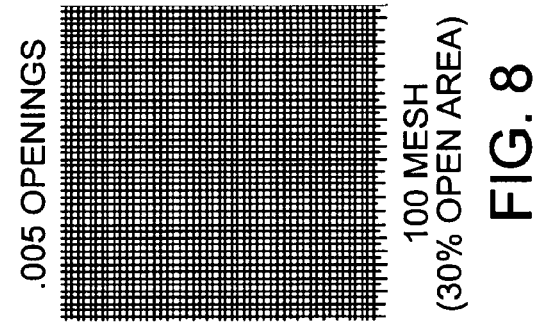
Figure 7:
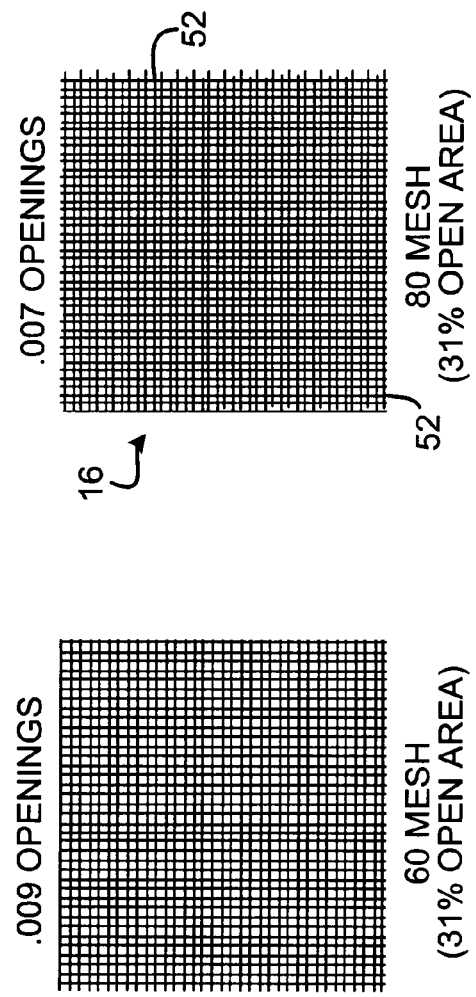
Figure 6:
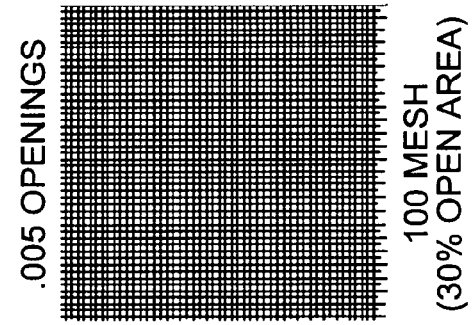

For example, a rotary knife cutter can be used to concurrently shear the fiber source 10 and screen the first fibrous material 12. Referring to FIG. 2, a rotary knife cutter 20 includes a hopper 22 that can be loaded with a shredded fiber source 10' prepared by shredding fiber source 10. Shredded fiber source 10' is sheared between stationary blades 24 and rotating blades 26 to provide a first fibrous material 12. First fibrous material 12 passes through screen 16 having the dimensions described above, and the resulting second fibrous material 14 is captured in bin 30. To aid in the collection of the second fibrous material 14, bin 30 can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source 50 (FIG. 2) is utilized to maintain the bin below nominal atmospheric pressure.

Shearing can be advantageous for "opening up" and "stressing" the fibrous materials, making the materials more dispersible, e.g., in a solution or in a resin, and making them more susceptible to chemical, enzymatic or biological attack. Without wishing to be bound by any particular theory, it is believed, at least in some embodiments, that shearing can functionalize fiber surfaces with functional groups, such as hydroxyl or carboxylic acid groups, which can, e.g., help disperse the fibers in a molten resin or enhance chemical or biological attack.

The fiber source can be sheared in a dry state, a hydrated state (e.g., having up to ten percent by weight absorbed water), or in a wet state, e.g., having between about 10 percent and about 75 percent by weight water. The fiber source can even be sheared while partially or fully submerged under a liquid, such as water, ethanol, isopropanol.

The fiber source can also be sheared in under a gas (such as a stream or atmosphere of gas other than air), e.g., oxygen or nitrogen, or steam.

Other methods of making the fibrous materials include stone grinding, mechanical ripping or tearing, pin grinding or air attrition milling.

If desired, the fibrous materials can be separated, e.g., continuously or in batches, into fractions according to their length, width, density, material type, or some combination of these attributes. For example, for forming composites, it is often desirable to have a relatively narrow distribution of fiber lengths. In addition, e.g., when making compositions that include bacteria and/or an enzyme, it is often desirable to use a substantially single material as a feedstock.

For example, ferrous materials can be separated from any of the fibrous materials by passing a fibrous material that includes a ferrous material past a magnet, e.g., an electromagnet, and then passing the resulting fibrous material through a series of screens, each screen having different sized apertures.

The fibrous materials can also be separated, e.g., by using a high velocity gas, e.g., air. In such an approach, the fibrous materials are separated by drawing off different fractions, which can be characterized photonically, if desired. Such a separation apparatus is discussed in Lindsey et al, U.S. Pat. No. 6,883,667, the entire disclosure of which is hereby incorporated by reference herein in its entirety.

The fibrous materials can be used immediately following their preparation, or they can may be dried, e.g., at approximately 105° C. for 4-18 hours, so that the moisture content is, e.g., less than about 0.5% before use.

If desired, lignin can be removed from any of the fibrous materials that include lignin, such as lignocellulosic materials. Also, if desired, the fibrous material can be sterilized to kill any microorganisms that may be on the fibrous material. For example, the fibrous material can be sterilized by exposing the fibrous material to radiation, such as infrared radiation, ultraviolet radiation, or an ionizing radiation, such as gamma radiation. The fibrous materials can also be sterilized by temperature adjustment, e.g., heating or cooling the fibrous material under conditions and for a sufficient time to kill any microorganisms, or by employing a chemical sterilant, such as bleach (e.g., sodium hypochlorite), chlorhexidine, or ethylene oxide. The fibrous materials can also be sterilized by using a competitive organism, such as yeast against bacteria.

Referring to FIGS. 3-8, in some embodiments, the average opening size of the first screen 16 is less than 0.79 mm (1/32 inch, 0.03125 inch), e.g., less than 0.51 mm (1/50 inch, 0.02000 inch), less than 0.40 mm (1/64 inch, 0.015625 inch), less than 0.23 mm (0.009 inch), less than 0.20 mm (1/128 inch, 0.0078125 inch), less than 0.18 mm (0.007 inch), less than 0.13 mm (0.005 inch), or even less than less than 0.10 mm (1/256 inch, 0.00390625 inch). Screen 16 is prepared by interweaving monofilaments 52 having an appropriate diameter to give the desired opening size. For example, the monofilaments can be made of a metal, e.g., stainless steel. As the opening sizes get smaller, structural demands on the monofilaments may become greater. For example, for opening sizes less than 0.40 mm, it can be advantageous to make the screens from monofilaments made from a material other than stainless steel, e.g., titanium, titanium alloys, amorphous metals, nickel, tungsten, rhodium, rhenium, ceramics, or glass. In some embodiments, the screen is made from a plate, e.g. a metal plate, having apertures, e.g., cut into the plate using a laser.

In some embodiments, the second fibrous 14 is sheared and passed through the first screen 16, or a different sized screen. In some embodiments, the second fibrous material 14 is passed through a second screen having an average opening size equal to or less than that of first screen 16.

Figure 9:
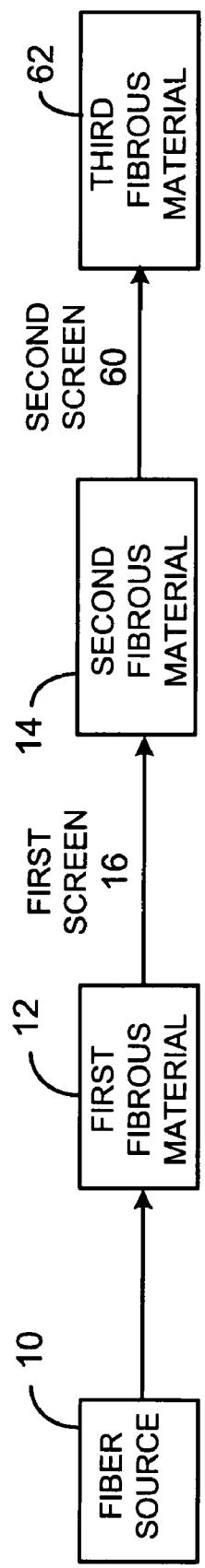
FIG. 9 is block diagram illustrating conversion of a fiber source into a first, second and third fibrous material.

Referring to FIG. 9, a third fibrous material 62 can be prepared from the second fibrous material 14 by shearing the second fibrous material 14 and passing the resulting material through a second screen 60 having an average opening size less than the first screen 16.

Figure 10B:
FIGS. 10A and 10B are photographs of fiber sources.
Figure 10A:

Fiber sources include cellulosic fiber sources, including paper and paper products like those shown in FIGS. 10A (polycoated paper) and 10B (Kraft paper), and lignocellulosic fiber sources, including wood, and wood-related materials, e.g., particle board. Other suitable fiber sources include natural fiber sources, e.g., grasses, rice hulls, bagasse, cotton, jute, hemp, flax, bamboo, sisal, abaca, straw, corn cobs, rice hulls, coconut hair; fiber sources high in α-cellulose content, e.g., cotton; synthetic fiber sources; e.g., extruded yarn (oriented yarn or un-oriented yarn) or carbon fiber sources; inorganic fiber sources; and metal fiber sources. Natural or synthetic fiber sources can be obtained from virgin scrap textile materials, e.g., remnants or they can be post consumer waste, e.g., rags. When paper products are used as fiber sources, they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Also, the fiber source can be obtained or derived from human (e.g., sewage), animal or plant wastes. Additional fiber sources have been described in U.S. Pat. Nos. 6,448,307, 6,258,876, 6,207,729, 5,973,035 and 5,952,105, each of which is incorporated by reference herein in its entirety.

Blends of any of the above fibrous sources may be used.

Generally, the fibers of the fibrous materials can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution. Without wishing to be bound by any particular theory, it is currently believed that the relatively large average length-to-diameter ratio and the relatively narrow length and/or length-to-diameter ratio distribution are, at least in part, responsible for the ease at which the fibrous materials are dispersed in a resin, e.g., a molten thermoplastic resin. It is also believed that the relatively large average length-to-diameter ratio and the relatively narrow length and/or length-to-diameter ratio distribution are, at least in part, responsible for the consistent properties of the fibrous materials, the predictable rheology modification the fibrous materials impart on a resin, the ease at which the combinations of the fibrous materials and resins are cast, extruded and injection molded, the ease in which the fibrous materials pass through small, often torturous channels and openings, and the excellent surface finishes possible with molded parts, e.g., glossy finishes and/or finishes substantially devoid of visible speckles.

As used herein, average fiber widths (i.e., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

The average length-to-diameter ratio of the second fibrous material 14 can be, e.g. greater than 8/1, e.g., greater than 10/1, greater than 15/1, greater than 20/1, greater than 25/1, or greater than 50/1. An average length of the second fibrous material 14 can be, e.g., between about 0.5 mm and 2.5 mm, e.g., between about 0.75 mm and 1.0 mm, and an average width (i.e., diameter) of the second fibrous material 14 can be, e.g., between about 5 μm and 50 μm, e.g., between about 10 μm and 30 μm.

In some embodiments, a standard deviation of the length of the second fibrous material 14 is less than 60 percent of an average length of the second fibrous material 14, e.g., less than 50 percent of the average length, less than 40 percent of the average length, less than 25 percent of the average length, less than 10 percent of the average length, less than 5 percent of the average length, or even less than 1 percent of the average length.

In some embodiments, a BET surface area of the second fibrous material 14 is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$. A porosity of the second fibrous material 14 can be, e.g., greater than 20 percent, greater than 25 percent, greater than 35 percent, greater than 50 percent, greater than 60 percent, greater than 70 percent, e.g., greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, a ratio of the average length-to-diameter ratio of the first fibrous material 12 to the average length-to-diameter ratio of the second fibrous material 14 is, e.g., less than 1.5, e.g., less than 1.4, less than 1.25, less than 1.1, less than 1.075, less than 1.05, less than 1.025, or even substantially equal to 1.

In particular embodiments, the second fibrous material 14 is sheared again and the resulting fibrous material passed through a second screen having an average opening size less than the first screen to provide a third fibrous material 62. In such instances, a ratio of the average length-to-diameter ratio of the second fibrous material 14 to the average length-to-diameter ratio of the third fibrous material 62 can be, e.g., less than 1.5, e.g., less than 1.4, less than 1.25, or even less than 1.1.

In some embodiments, the third fibrous material 62 is passed through a third screen to produce a fourth fibrous material. The fourth fibrous material can be, e.g., passed through a fourth screen to produce a fifth material. Similar screening processes can be repeated as many times as desired to produce the desired fibrous material having the desired properties.

In some embodiments, the desired fibrous material includes fibers having an average length-to-diameter ratio of greater than 5 and having a standard deviation of the fiber length that is less than sixty percent of the average length. For example, the average length-to-diameter ratio can be greater than 10/1, e.g., greater than 25/1, or greater than 50/1, and the average length can be between about 0.5 mm and 2.5 mm, e.g., between about 0.75 mm and 1.0 mm. An average width of the fibrous material can be between about 5 µm and 50 µm, e.g., between about 10 µm and 30 µm. For example, the standard deviation can be less than 50 percent of the average length, e.g., less than 40 percent, less than 30 percent, less than 25 percent, less than 20 percent, less than 10 percent, less than 5 percent, or even less than 1 percent of the average length. A desirable fibrous material can have, e.g., a BET surface area of greater than 0.5 $m^2/g$, e.g., greater than 1.0 $m^2/g$, greater than 1.5 $m^2/g$, greater than 1.75 $m^2/g$., greater than 5 $m^2/g$, greater than 10 $m^2/g$, greater than 25.0 $m^2/g$, greater than 50.0 $m^2/g$, greater than 75.0 $m^2/g$, or even greater than 100.0 $m^2/g$. A desired material can have, e.g., a porosity of greater than 70 percent, e.g., greater than 80 percent, greater than 87.5 percent, greater than 90 percent, greater than 92.5, greater than 95, greater than 97.5, or even greater than 99 percent. A particularly preferred embodiment has a BET surface area of greater than 1.25 $m^2/g$ and a porosity of greater than 85 percent.

Fibrous Material/Resin Composites

Composites including any of the fibrous materials or blends of any of the fibrous materials described herein (including any of the fibrous materials disclosed in U.S. Pat. Nos. 6,448,307, 6,258,876, 6,207,729, 5,973,035 and 5,952,105), e.g., the first 12 or second fibrous material 14, and a resin, e.g., a thermoplastic resin or a thermosetting resin, can be prepared by combining the desired fibrous material and the desired resin. The desired fibrous material can be combined with the desired resin, e.g., by mixing the fibrous material and the resin in an extruder or other mixer. To form the composite, the fibrous material can be combined with the resin as the fibrous material itself or as a densified fibrous material that can be re-opened during the combining. Such a densified material is discussed in International Application No. PCT/US2006/010648, filed on Mar. 23, 2006, the disclosure of which is incorporated herein by reference in its entirety.

Examples of thermoplastic resins include rigid and elastomeric thermoplastics. Rigid thermoplastics include polyolefins (e.g., polyethylene, polypropylene, or polyolefin copolymers), polyesters (e.g., polyethylene terephthalate), polyamides (e.g., nylon 6, 6/12 or 6/10), and polyethyleneimines. Examples of elastomeric thermoplastic resins include elastomeric styrenic copolymers (e.g., styrene-ethylene-butylene-styrene copolymers), polyamide elastomers (e.g., polyether-polyamide copolymers) and ethylene-vinyl acetate copolymer.

In some embodiments, the thermoplastic resin has a melt flow rate of between 10 g/10 minutes to 60 g/10 minutes, e.g., between 20 g/10 minutes to 50 g/10 minutes, or between 30 g/10 minutes to 45 g/10 minutes, as measured using ASTM 1238.

In some embodiments, compatible blends of any of the above thermoplastic resins can be used.

In some embodiments, the thermoplastic resin has a polydispersity index (PDI), i.e., a ratio of the weight average molecular weight to the number average molecular weight, of greater than 1.5, e.g., greater than 2.0, greater than 2.5, greater than 5.0, greater than 7.5, or even greater than 10.0.

In specific embodiments, polyolefins or blends of polyolefins are utilized as the thermoplastic resin.

Examples of thermosetting resins include natural rubber, butadiene-rubber and polyurethanes.

In addition to the desired fibrous material and resin, additives, e.g., in the form of a solid or a liquid, can be added to the combination of the fibrous material and resin. For example, suitable additives include fillers such as calcium carbonate, graphite, wollastonite, mica, glass, fiber glass, silica, and talc; inorganic flame retardants such as alumina trihydrate or magnesium hydroxide; organic flame retardants such as chlorinated or brominated organic compounds; ground construction waste; ground tire rubber; carbon fibers; or metal fibers or powders (e.g., aluminum, stainless steel). These additives can reinforce, extend, or change electrical, mechanical or compatibility properties. Other additives include fragrances, coupling agents, compatibilizers, e.g., maleated polypropylene, processing aids, lubricants, e.g., fluorinated polyethylene, plasticizers, antioxidants, opacifiers, heat stabilizers, colorants, foaming agents, impact modifiers, polymers, e.g., degradable polymers, photostabilizers, biocides, antistatic agents, e.g., stearates or ethoxylated fatty acid amines. Suitable antistatic compounds include conductive carbon blacks, carbon fibers, metal fillers, cationic compounds, e.g., quaternary ammonium compounds, e.g., N-(3-chloro-2-hydroxypropyl)trimethylammonium chloride, alkanolamides, and amines. Representative degradable polymers include polyhydroxy acids, e.g., polylactides, polyglycolides and copolymers of lactic acid and glycolic acid, poly(hydroxybutyric acid), poly(hydroxyvaleric acid), poly[lactide-co-(e-caprolactone)], poly[glycolide-co-(e-caprolactone)], polycarbonates, poly(amino acids), poly(hydroxyalkanoate)s, polyanhydrides, polyorthoesters and blends of these polymers.

In some embodiments, the fibrous material is sterilized prior to combining with a resin to kill any microorganisms that may be on the fibrous material. For example, the fibrous material can be sterilized by exposing the fibrous material to radiation; by heating the fibrous material under conditions and for a sufficient time to kill any microorganisms, e.g., boiling at normal atmospheric pressure; or by employing chemical sterilants.

It can be advantageous to make the composite smell and/or look like natural wood, e.g., cedarwood. For example, the fragrance, e.g., natural wood fragrance, can be compounded into the resin used to make the composite. In some implementations, the fragrance is compounded directly into the resin as an oil. For example, the oil can be compounded into the resin using a roll mill, e.g., a Banbury® mixer or an extruder, e.g., a twin-screw extruder with counter-rotating screws. An example of a Banbury® mixer is the F-Series Banbury® mixer, manufactured by Farrel. An example of a twin-screw extruder is the WP ZSK 50 MEGAcompunder™, manufactured by Krupp Werner & Pfleiderer. After compounding, the scented resin can be added to the fibrous material and extruded or molded. Alternatively, master batches of fragrance-filled resins are available commercially from International Flavors and Fragrances, under the tradename PolyIff™ or from the RTP Company. In some embodiments, the amount of fragrance in the composite is between about 0.005% by weight and about 10% by weight, e.g., between about 0.1% and about 5% or 0.25% and about 2.5%.

Other natural wood fragrances include evergreen or redwood. Other fragrances include peppermint, cherry, strawberry, peach, lime, spearmint, cinnamon, anise, basil, bergamot, black pepper, camphor, chamomile, citronella, eucalyptus, pine, fir, geranium, ginger, grapefruit, jasmine, juniperberry, lavender, lemon, mandarin, marjoram, musk, myrrh, orange, patchouli, rose, rosemary, sage, sandalwood, tea tree, thyme, wintergreen, ylang ylang, vanilla, new car or mixtures of these fragrances. In some embodiments, the amount of fragrance in the fibrous material-fragrance combination is between about 0.005% by weight and about 20% by weight, e.g., between about 0.1% and about 5% or 0.25% and about 2.5%. Even other fragrances and methods are described U.S. Provisional application Ser. No. 60/688,002, filed Jun. 7, 2005, the entire disclosure of which is hereby incorporated by reference herein.

Any of the fibrous material described above, e.g., the first 12 or second fibrous material 14, together with a resin, can be used to form articles such as pipes, panels, decking materials, boards, housings, sheets, blocks, bricks, poles, fencing, members, doors, shutters, awnings, shades, signs, frames, window casings, backboards, flooring, tiles, railroad ties, trays, tool handles, stalls, films, wraps, tapes, boxes, baskets, racks, casings, binders, dividers, walls, mats, frames, bookcases, sculptures, chairs, tables, desks, toys, games, pallets, wharves, piers, boats, masts, septic tanks, automotive panels, computer housings, above- and below-ground electrical casings, furniture, picnic tables, benches, shelters, trays, hangers, servers, caskets, book covers, canes, crutches, insulation, thread, cloth, novelties, house wares and structures.

The fibrous material may be dyed before combining with the resin and compounding to form the composites described above. In some embodiments, this dyeing can be helpful in masking or hiding the fibrous material, especially large agglomerations of the fibrous material, in molded or extruded parts. Such large agglomerations, when present in relatively high concentrations, can show up as speckles in the surfaces of the molded or extruded parts.

For example, the desired fibrous material can be dyed using an acid dye, direct dye or a reactive dye. Such dyes are available from Spectra Dyes, Kearny, N.J. or Keystone Aniline Corporation, Chicago, Ill. Specific examples of dyes include SPECTRA™ LIGHT YELLOW 2G, SPECTRACID™ YELLOW 4GL CONC 200, SPECTRANYL™ RHODAMINE 8, SPECTRANYL™ NEUTRAL RED B, SPECTRAMINE™ BENZOPERPURINE, SPECTRADIAZO™ BLACK OB, SPECTRAMINE™ TURQUOISE G, and SPECTRAMINE™ GREY LVL 200%, each being available from Spectra Dyes.

In some embodiments, resin color concentrates containing pigments are blended with dyes. When such blends are then compounded with the desired fibrous material, the fibrous material may be dyed in-situ during the compounding. Color concentrates are available from Clariant.

EXAMPLES

Scanning electron micrographs were obtained on a JEOL 65000 field emission scanning electron microscope. Fiber lengths and widths (i.e., diameters) were determined by Integrated Paper Services, Inc., Appleton, Wis., using an automated analyzer (TAPPI T271). BET surface area was determined by Micromeritics Analytical Services, as were porosity and bulk density.

Example 1

Preparation of Fibrous Material from Polycoated Paper

Figure 11:
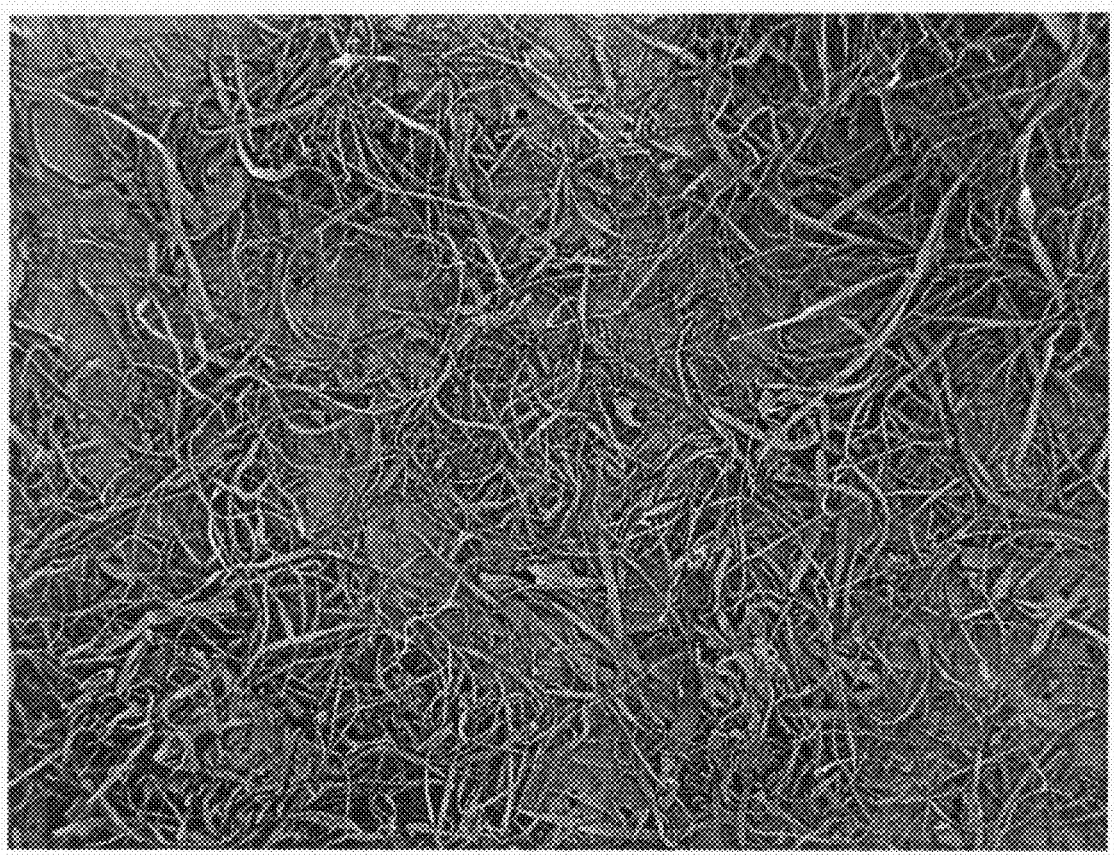
FIGS. 11 and 12 are scanning electron micrographs of a fibrous material produced from polycoated paper at 25× magnification and 1000× magnification, respectively. The fibrous material was produced on a rotary knife cutter utilizing a screen with ⅛ inch openings.
Figure 12:
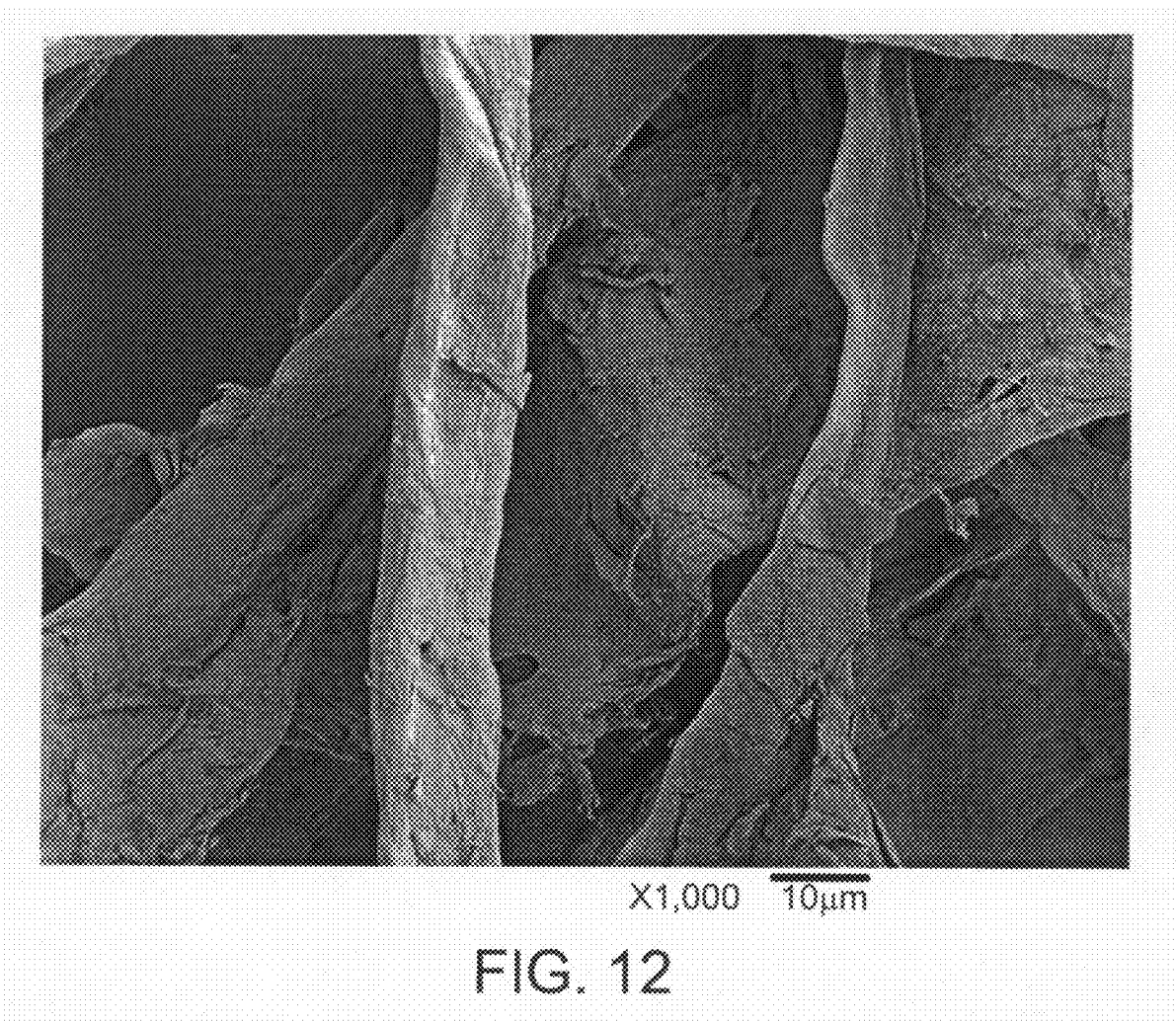

A 1500 pound skid of virgin, half-gallon juice cartons made of un-printed polycoated white Kraft board having a bulk density of 20 lb/ft$^3$ was obtained from International Paper. The material was cut into pieces 8¼ inches by 11 inches using a guillotine cutter and fed to a Munson rotary knife cutter, Model SC30. Model SC30 is equipped with four rotary blades, four fixed blades, and a discharge screen having ⅛ inch openings. The gap between the rotary and fixed blades was set to approximately 0.020 inch. The rotary knife cutter sheared the confetti-like pieces across the knife-edges, tearing the pieces apart and releasing a fibrous material at a rate of about one pound per hour. The fibrous material had a BET surface area of 0.9748 m$^2$/g +/±0.0167 m$^2$/g, a porosity of 89.0437 percent and a bulk density (@0.53 psia) of 0.1260 g/mL. An average length of the fibers was 1.141 mm and an average width of the fibers was 0.027 mm, giving an average L/D of 42:1. Scanning electron micrographs of the fibrous material are shown in FIGS. 11 and 12 at 25× magnification and 1000× magnification, respectively.

Example 2

Preparation of Fibrous Material from Bleached Kraft Board

Figure 13:
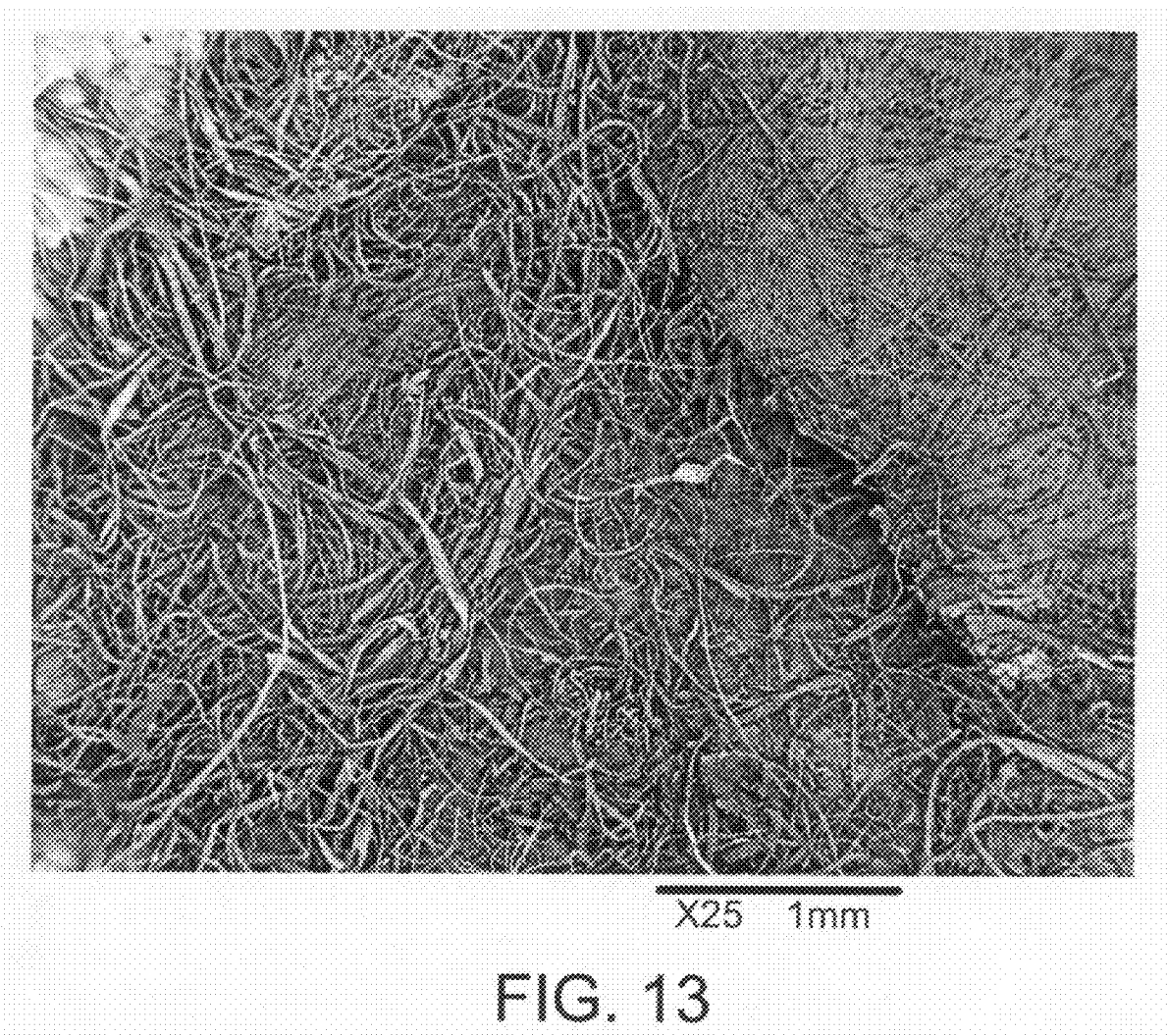
FIGS. 13 and 14 are scanning electron micrographs of a fibrous material produced from bleached Kraft board paper at 25× magnification and 1000× magnification, respectively. The fibrous material was produced on a rotary knife cutter utilizing a screen with ⅛ inch openings.
Figure 14:
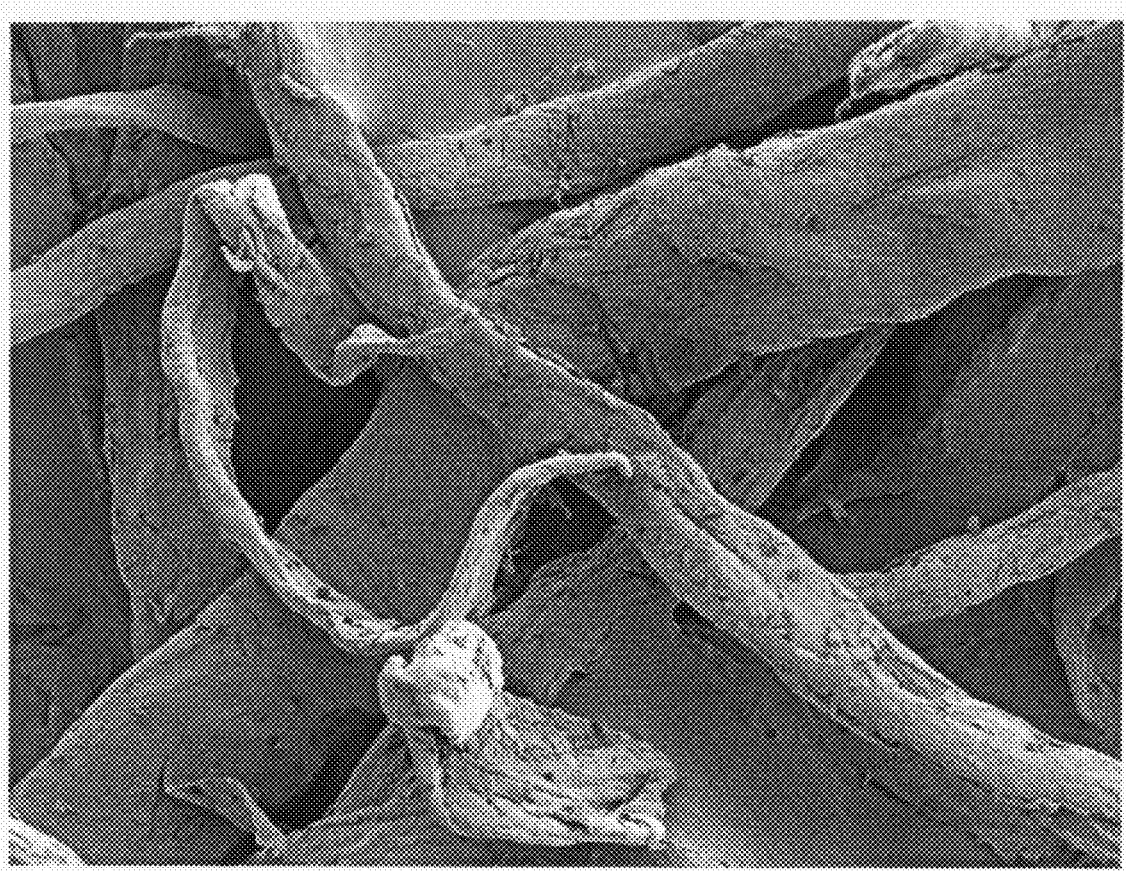

A 1500 pound skid of virgin bleached white Kraft board having a bulk density of 30 lb/ft$^3$ was obtained from International Paper. The material was cut into pieces 8¼ inches by 11 inches using a guillotine cutter and fed to a Munson rotary knife cutter, Model SC30. The discharge screen had ⅛ inch openings. The gap between the rotary and fixed blades was set to approximately 0.020 inch. The rotary knife cutter sheared the confetti-like pieces, releasing a fibrous material at a rate of about one pound per hour. The fibrous material had a BET surface area of 1.1316 m$^2$/g+/−0.0103 m$^2$/g, a porosity of 88.3285 percent and a bulk density (@0.53 psia) of 0.1497 g/mL. An average length of the fibers was 1.063 mm and an average width of the fibers was 0.0245 mm, giving an average L/D of 43:1. Scanning electron micrographs of the fibrous material are shown in FIGS. 13 and 14 at 25× magnification and 1000× magnification, respectively.

Example 3

Preparation of Twice Sheared Fibrous Material from Bleached Kraft Board

Figure 15:
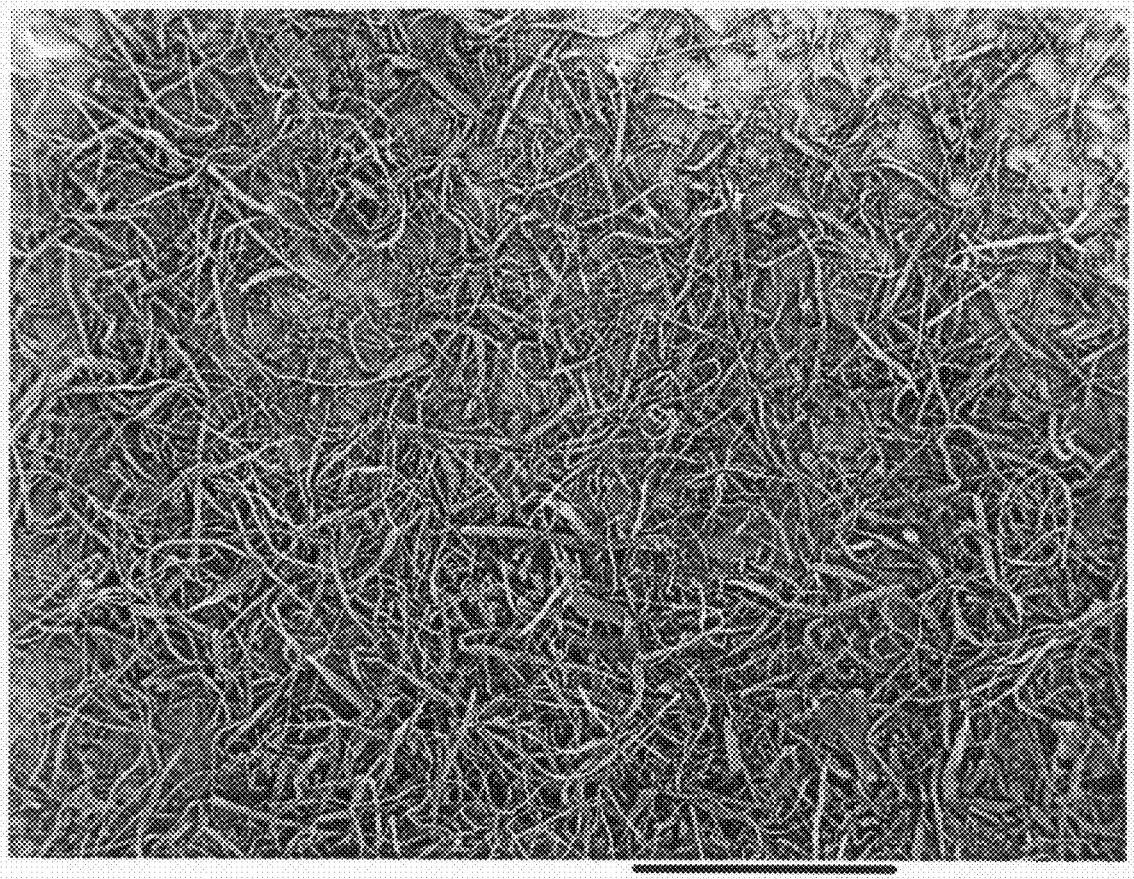
FIGS. 15 and 16 are scanning electron micrographs of a fibrous material produced from bleached Kraft board paper at 25× magnification and 1000× magnification, respectively. The fibrous material was twice sheared on a rotary knife cutter utilizing a screen with 1/16 inch openings during each shearing.
Figure 16:
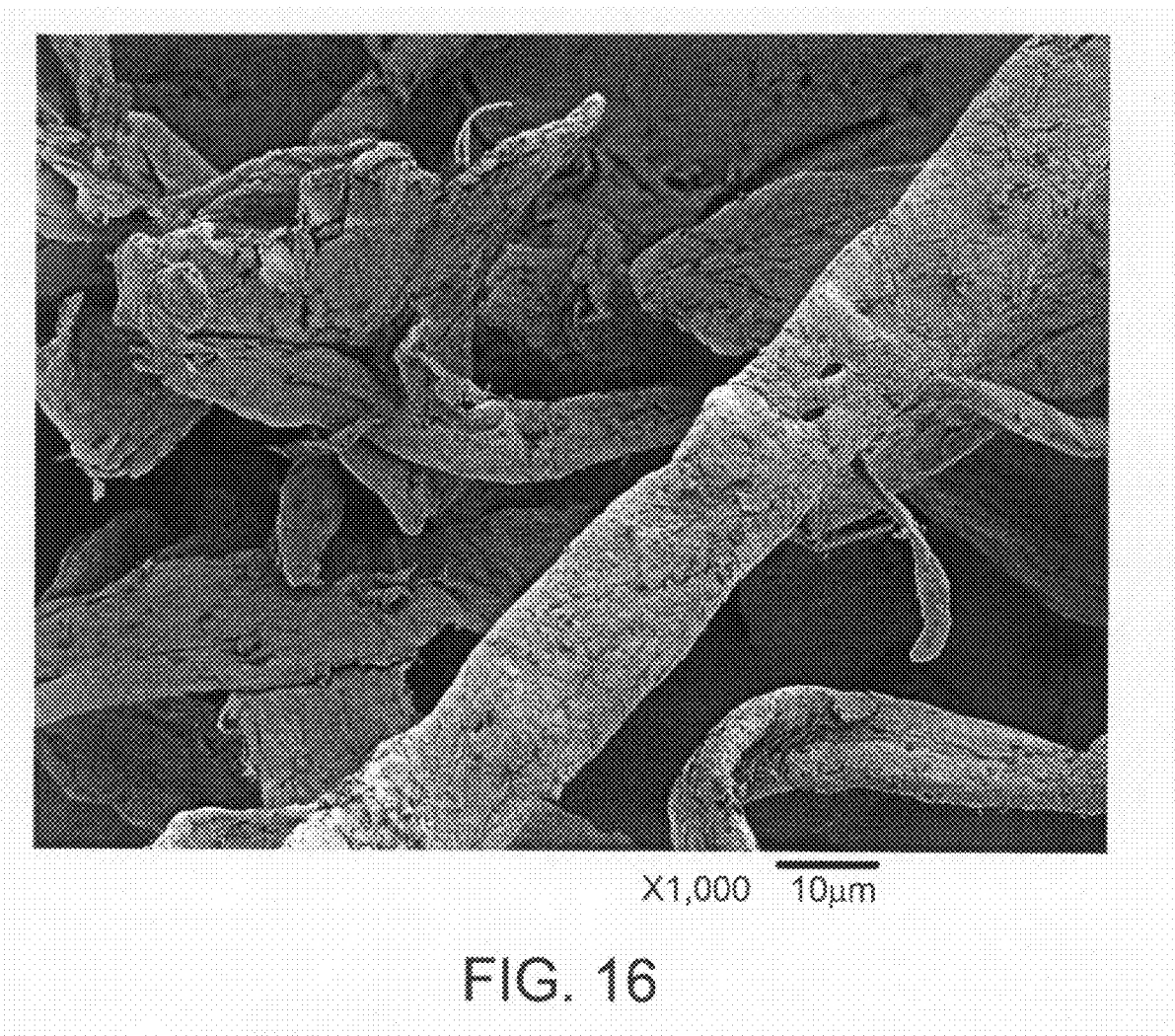

A 1500 pound skid of virgin bleached white Kraft board having a bulk density of 30 lb/ft$^3$ was obtained from International Paper. The material was cut into pieces 8¼ inches by 11 inches using a guillotine cutter and fed to a Munson rotary knife cutter, Model SC30. The discharge screen had 1/16 inch openings. The gap between the rotary and fixed blades was set to approximately 0.020 inch. The rotary knife cutter the confetti-like pieces, releasing a fibrous material at a rate of about one pound per hour. The material resulting from the first shearing was fed back into the same setup described above and sheared again. The resulting fibrous material had a BET surface area of 1.4408 m$^2$/g+/−0.0156 m$^2$/g, a porosity of 90.8998 percent and a bulk density (@0.53 psia) of 0.1298 g/mL. An average length of the fibers was 0.891 mm and an average width of the fibers was 0.026 mm, giving an average L/D of 34:1. Scanning electron micrographs of the fibrous material are shown in FIGS. 15 and 16 at 25× magnification and 1000× magnification, respectively.

Example 4

Preparation of Thrice Sheared Fibrous Material from Bleached Kraft Board

Figure 17:
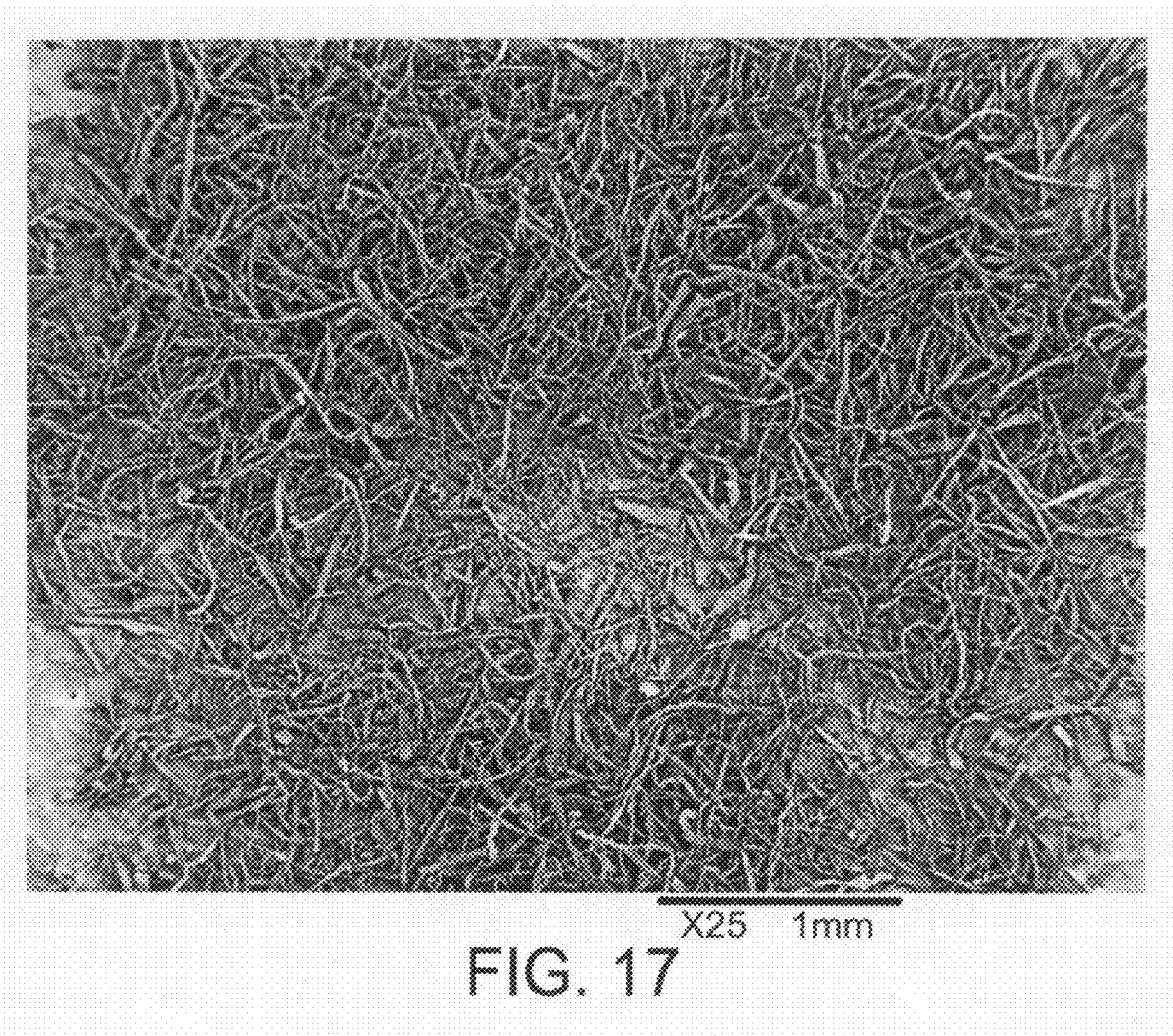
FIGS. 17 and 18 are scanning electron micrographs of a fibrous material produced from bleached Kraft board paper at 25× magnification and 1000× magnification, respectively. The fibrous material was thrice sheared on a rotary knife cutter. During the first shearing, a ⅛ inch screen was used; during the second shearing, a 1/16 inch screen was used, and during the third shearing a 1/32 inch screen was used.
Figure 18:
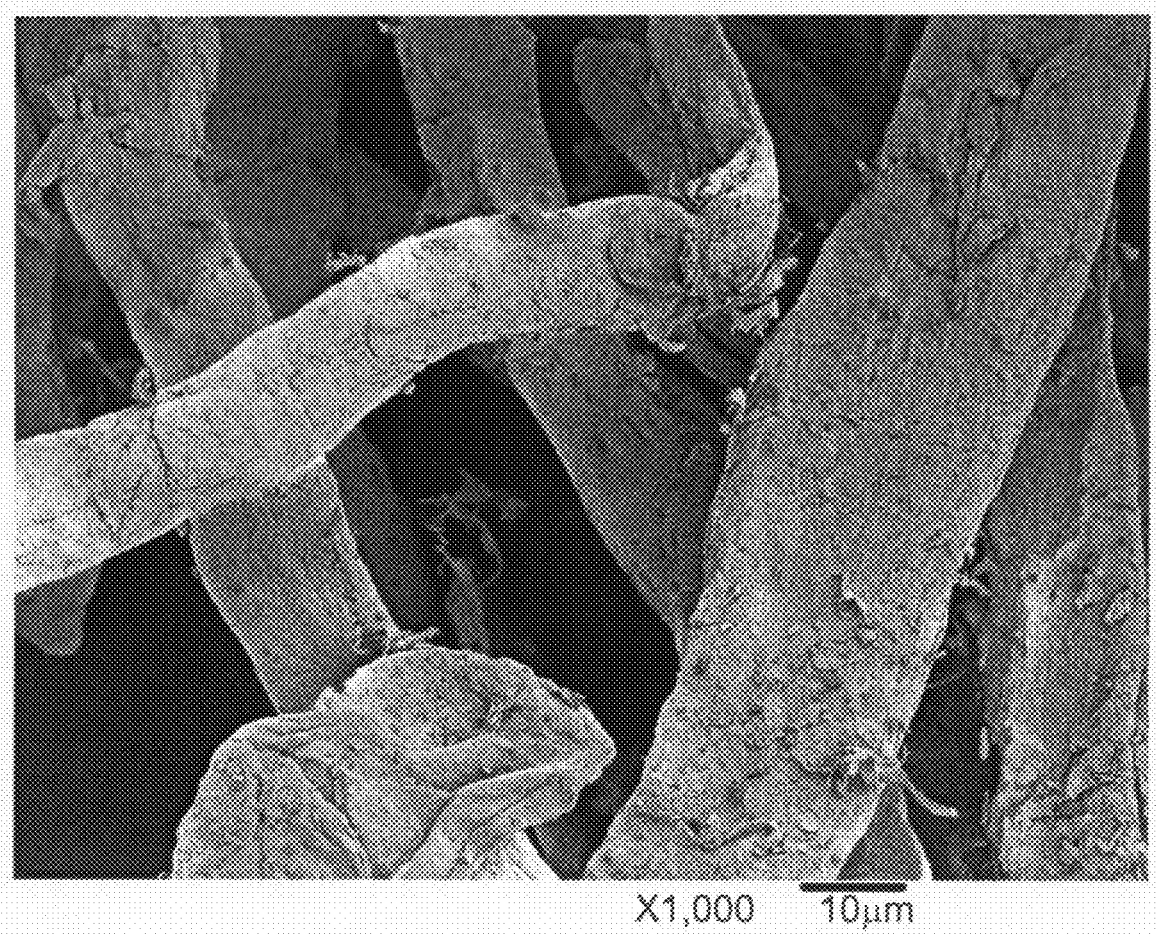

A 1500 pound skid of virgin bleached white Kraft board having a bulk density of 30 lb/ft$^3$ was obtained from International Paper. The material was cut into pieces 8¼ inches by 11 inches using a guillotine cutter and fed to a Munson rotary knife cutter, Model SC30. The discharge screen had ⅛ inch openings. The gap between the rotary and fixed blades was set to approximately 0.020 inch. The rotary knife cutter sheared the confetti-like pieces across the knife-edges. The material resulting from the first shearing was fed back into the same setup and the screen was replaced with a 1/16 inch screen. This material was sheared. The material resulting from the second shearing was fed back into the same setup and the screen was replaced with a 1/32 inch screen. This material was sheared. The resulting fibrous material had a BET surface area of 1.6897 m$^2$/g+/−0.0155 m$^2$/g, a porosity of 87.7163 percent and a bulk density (@0.53 psia) of 0.1448 g/mL. An average length of the fibers was 0.824 mm and an average width of the fibers was 0.0262 mm, giving an average L/D of 32:1. Scanning electron micrographs of the fibrous material are shown in FIGS. 17 and 18 at 25× magnification and 1000× magnification, respectively.

Other Compositions and Uses of the Fibrous Materials

Compositions can be prepared that include any of the fibrous materials described herein, including any of the fibrous materials, resins, additives or other components disclosed in U.S. Pat. Nos. 6,448,307, 6,258,876, 6,207,729, 5,973,035 and 5,952,105). For example, any of the fibrous materials described herein can be combined with a solid, a liquid or a gas, e.g., a chemical or chemical formulation (in the solid or liquid state), such as a pharmaceutical (e.g., an antibiotic), an agricultural material (e.g., plant seeds, a fertilizer, herbicide or pesticide), or an enzyme or a formulation that includes enzymes. Compositions that include one or more type of bacteria or bacteria in combination with one or more enzymes can also be prepared.

Such compositions can take advantage of the fibrous material's desirable properties. For example, any of the fibrous materials can be used to absorb chemicals, potentially absorbing many times their own weight. For example, the fibrous materials can be used to absorb spilled oil, or other chemicals. Combining these fibrous materials with a microorganism, such as a bacterium, that can metabolize the oil or chemical can aid in cleanup. For example, the fibrous materials can be combined with solutions of enzymes, dried, and then used in pet bedding, or combined with a pharmaceutical and used for delivering a therapeutic agent, such as a drug. If desired, the fibrous materials can be combined with a degradable polymer, e.g., polyglycolic acid, polylactic acid and copolymers of glycolic and lactic acid. Other degradable materials that can be used have been discussed above.

Compositions that include fibrous materials, e.g., cellulosic or lignocellulosic materials and, e.g., chemicals or chemical formulations in the solid, liquid or gaseous state, can be prepared, e.g., in various immersion, spraying, or blending apparatuses. For example, the compositions can be prepared using ribbon blenders, cone blenders, double cone blenders, and Patterson-Kelly "V" blenders.

If desired, lignin can be removed from any of the fibrous materials that include lignin, such as lignocellulosic materials. Also, if desired, the fibrous material can be sterilized to kill any microorganisms that may be on the fibrous material. For example, the fibrous material can be sterilized by exposing the fibrous material to radiation, such as infrared radiation, ultraviolet radiation, or an ionizing radiation, such as gamma radiation. The fibrous materials can also be sterilized by heating the fibrous material under conditions and for a sufficient time to kill any microorganisms, or by employing a chemical sterilant, such as bleach (e.g., sodium hypochlorite), chlorhexidine, or ethylene oxide.

Any of the fibrous materials can be washed, e.g., with a liquid such as water, to remove any undesirable impurities and/or contaminants.

In a specific application, the fibrous materials can be used as a feedstock for various microorganisms, such as yeast and bacteria, that can ferment or otherwise work on the fibrous materials to produce a useful material, such as a fuel, e.g., an alcohol, an organic acid, a hydrocarbon or hydrogen, or a protein.

The alcohol produced can be a monohydroxy alcohol, e.g., ethanol, or a polyhydroxy alcohol, e.g., ethylene glycol or glycerin. Examples of alcohols that can be produced include methanol, ethanol, propanol, isopropanol, butanol, ethylene glycol, propylene glycol, 1,4-butane diol, glycerin or mixtures of these alcohols. The organic acid produced can a monocarboxylic acid or a polycarboxylic acid. Examples of organic acids include formic acid, acetic acid, propionic acid, butyric acid, valeric acid, caproic, palmitic acid, stearic acid, oxalic acid, malonic acid, succinic acid, glutaric acid, oleic acid, linoleic acid, glycolic acid, lactic acid, γ-hydroxybutyric acid or mixtures of these acids. The hydrocarbon produced can be, e.g., an alkane or an alkene. Examples of hydrocarbons that can be produced include methane, ethane, propane, isobutene, pentane, n-hexane or mixtures of these hydrocarbons.

In a particular embodiment, a fiber source that includes a cellulosic and/or lignocellulosic fiber source is sheared to provide a first fibrous material. The first fibrous material is then passed through a first screen having an average opening size of about 1.59 mm or less (1/16 inch, 0.0625 inch) to provide a second fibrous material. The second fibrous material is combined with a bacterium and/or enzyme. In this particular embodiment, the bacterium and/or enzyme is capable of utilizing the second fibrous material directly without pre-treatment to produce a fuel that includes hydrogen, an alcohol, an organic acid and/or a hydrocarbon.

In some embodiments, prior to combining the bacteria and/or enzyme, the fibrous material is sterilized to kill any microorganisms that may be on the fibrous material. For example, the fibrous material can be sterilized by exposing the fibrous material to radiation, such as infrared radiation, ultraviolet radiation, or an ionizing radiation, such as gamma radiation. The microorganisms can also be killed using chemical sterilants, such as bleach (e.g., sodium hypochlorite), chlorhexidine, or ethylene oxide.

In a particular embodiment, the cellulosic and/or lignocellulosic material of the fibrous material is first broken down into lower molecular weight sugars, which are then added to a solution of yeast and/or bacteria that ferment the lower molecular weight sugars to produce ethanol. The cellulosic and/or lignocellulosic material can be broken down using chemicals, such as acids or bases, by enzymes, or by a combination of the two. Chemical hydrolysis of cellulosic materials is described by Bjerre, in *Biotechnol. Bioeng.*, 49:568 (1996) and Kim in *Biotechnol. Prog.*, 18:489 (2002), which are each hereby incorporated by reference herein in their entirety.

Bioethanol strategies are discussed by DiPardo in *Journal of Outlook for Biomass Ethanol Production and Demand (EIA Forecasts)*, 2002; Sheehan in *Biotechnology Progress*, 15:8179, 1999; Martin in *Enzyme Microbes Technology*, 31:274, 2002; Greer in *BioCycle*, 61-65, April 2005; Lynd in *Microbiology and Molecular Biology Reviews*, 66:3, 506-577, 2002; Ljungdahl et al. in U.S. Pat. No. 4,292,406; and Bellamy in U.S. Pat. No. 4,094,742, which are each hereby incorporated by reference herein in their entirety.

Figure 19:
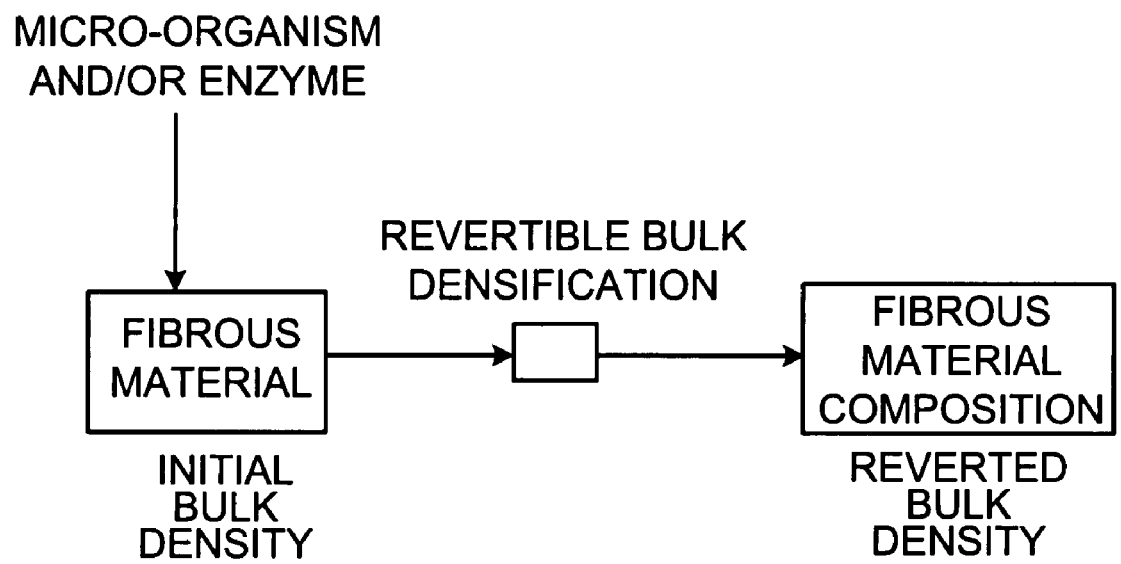
FIG. 19 is a block diagram illustrating revertible bulk densification of a fibrous material composition.

Referring now to FIG. 19, a fibrous material having a low bulk density can be combined with a microorganism, e.g., freeze-dried yeast or bacteria, and/or a enzyme, and then revertibly densified to a fibrous material composition having a higher bulk density. For example, a fibrous material composition having a bulk density of 0.05 g/cm$^3$ can be densified by sealing the fibrous material in a relatively gas impermeable structure, e.g., a bag made of polyethylene or a bag made of alternating layers of polyethylene and a nylon, and then evacuating the entrapped gas, e.g., air, from the structure. After evacuation of the air from the structure, the fibrous material can have, e.g., a bulk density of greater than 0.3 g/cm$^3$, e.g., 0.5 g/cm$^3$, 0.6 g/cm$^3$, 0.7 g/cm$^3$ or more, e.g., 0.85 g/cm$^3$. This can be advantageous when it is desirable to transport the fibrous material to another location, e.g., a remote manufacturing plant, where the fibrous material composition can be added to a solution, e.g., to produce ethanol. After piercing the substantially gas impermeable structure, the densified fibrous material reverts to nearly its initial bulk density, e.g., greater than 60 percent of its initial bulk density, e.g., 70 percent, 80 percent, 85 percent or more, e.g., 95 percent of its initial bulk density. To reduce static electricity in the fibrous material, an anti-static agent can be added to the fibrous material. For example, a chemical anti-static compound, e.g., a cationic compound, e.g., quaternary ammonium compound, can be added to the fibrous material.

In some embodiments, the structure, e.g., bag, is formed of a material that dissolves in a liquid, such as water. For example, the structure can be formed from a polyvinyl alcohol so that it dissolves when in contact with a water-based system. Such embodiments allow densified structures to be added directly to solutions, e.g., that include a microorganism, without first releasing the contents of the structure, e.g., by cutting.

Other Embodiments

While certain embodiments have been described, other embodiments are possible.

While some embodiments use screens to provide a desired fibrous material, in some embodiments, no screens are used to make the desired fibrous. For example, in some embodiments, a fiber source is sheared between a first pair of blades that defines a first gap, resulting in a first fibrous material. The first fibrous material is then sheared between a second pair of blades that define a second gap that is smaller than the first gap, resulting in a second fibrous material. Similar screening processes can be repeated as many times as desired to produce the desired fibrous material having the desired properties.

In some embodiments, a ratio of an average length-to-diameter ratio of the first fibrous material to an average length-to-diameter of the second fibrous material is less than 1.5.

Still other embodiments are within the scope of the following claims.

What I claim is:

1. A method comprising:
    passing a first fibrous material that has been prepared by shearing a cellulosic or lignocellulosic fiber source through a first screen having an average opening size of 1.59 mm or less (1/16 inch; 0.0625 inch) to provide a second fibrous material having a BET surface area greater than 0.25 m$^2$/g and a porosity greater than 25 percent.

2. The method of claim 1, wherein the fiber source has been subjected to cutting prior to shearing the fiber source.

3. The method of claim 1, wherein the shearing was performed with a rotary knife cutter.

4. The method of claim 1, further comprising shearing the sheared and screened fibrous material.

5. The method of claim 1, further comprising shearing the sheared and screened fibrous material, and passing the resulting fibrous material through the first screen.

6. The method of claim 1, further comprising shearing the sheared and screened fibrous material, and passing the resulting fibrous material through a second screen having an average opening size less than the first screen.

7. The method of claim 1, wherein the shearing of the fiber source and the passing of the first fibrous material through the first screen are performed concurrently.

8. The method of claim 1, wherein an average length-to-diameter ratio of fibers of the second fibrous material is greater than 8/1.

9. The method of claim 1, wherein a standard deviation of a length of fibers of the second fibrous material is less than 60 percent of an average length of fibers of the second fibrous material.

10. The method of claim 1, wherein a ratio of an average length-to-diameter ratio of fibers of the first fibrous material to an average length-to-diameter ratio of the second fibrous material is less than 1.5.

11. The method of claim 1, wherein the fiber source comprises a cellulosic material or a lignocellulosic material.

12. The method of claim 1, wherein the first screen has an average opening size of 0.79 mm or less (1/32 inch, 0.03125 inch).

13. The method of claim 1, wherein the BET surface area is greater than 0.4 m$^2$/g.

14. The method of claim 13, wherein the BET surface area is greater than 1.0 m$^2$/g.

15. The method of claim 1, further comprising combining the second fibrous material with bacterium and/or enzyme.

16. The method of claim 15, wherein the fibrous material is passed through a second screen before combining the fibrous material with the bacterium and/or enzyme.

* * * * *